(12) United States Patent
Farber et al.

(10) Patent No.: US 9,662,367 B2
(45) Date of Patent: May 30, 2017

(54) ADAPTOGENIC COMPOSITIONS AND METHOD FOR PRODUCTION THEREOF

(71) Applicant: Rubikon Ltd., Vitebsk (BY)

(72) Inventors: Viktar Farber, Vitebsk (BY); Viatcheslav Smetanin, Vitebsk (BY); Alena Hukava, Vitebsk (BY); Andrei Mastykau, Vitebsk (BY)

(73) Assignee: Rubikon Ltd., Vitebsk (BY)

( * ) Notice: Subject to any disclaimer, the term of this patent is extended or adjusted under 35 U.S.C. 154(b) by 0 days.

(21) Appl. No.: 14/815,243

(22) Filed: Jul. 31, 2015

(65) Prior Publication Data

US 2016/0030499 A1    Feb. 4, 2016

Related U.S. Application Data

(60) Provisional application No. 62/032,307, filed on Aug. 1, 2014.

(51) Int. Cl.

| A61K 36/79 | (2006.01) |
|---|---|
| A61K 31/09 | (2006.01) |
| A61K 9/48 | (2006.01) |
| A61K 31/00 | (2006.01) |

(52) U.S. Cl.
CPC .......... *A61K 36/79* (2013.01); *A61K 9/485* (2013.01); *A61K 9/4858* (2013.01); *A61K 9/4866* (2013.01); *A61K 31/00* (2013.01); *A61K 31/09* (2013.01); *A61K 2236/00* (2013.01)

(58) Field of Classification Search
CPC .... A61K 2236/00; A61K 31/09; A61K 36/79; A61K 9/485; A61K 9/4858; A61K 9/4866
See application file for complete search history.

(56) References Cited

U.S. PATENT DOCUMENTS

| 4,466,923 A | 8/1984 | Friedrich |
|---|---|---|
| 5,589,182 A | 12/1996 | Tashiro et al. |
| 5,770,207 A | 6/1998 | Bewicke |
| 5,770,217 A | 6/1998 | Kutilek, III et al. |
| 6,280,751 B1 | 8/2001 | Fletcher et al. |
| 8,142,830 B2 | 3/2012 | Marentis |
| 8,252,312 B1 | 8/2012 | Wong et al. |
| 2002/0006444 A1 | 1/2002 | Konishi |
| 2003/0203050 A1 | 10/2003 | Sherwood et al. |
| 2003/0206978 A1 | 11/2003 | Sherwood et al. |
| 2004/0147605 A1 | 7/2004 | Onuki et al. |
| 2007/0020345 A1 | 1/2007 | Ko |
| 2007/0065524 A1 | 3/2007 | Wang |
| 2007/0128302 A1* | 6/2007 | Henry ............... A61K 8/97 424/777 |
| 2007/0264367 A1 | 11/2007 | Kim |
| 2008/0196299 A1 | 8/2008 | Anitescu et al. |
| 2008/0305096 A1 | 12/2008 | Verdegem et al. |
| 2009/0011013 A1 | 1/2009 | Ranklove et al. |
| 2009/0011112 A1 | 1/2009 | Marentis |
| 2009/0169652 A1 | 7/2009 | Osborne |
| 2009/0169653 A1 | 7/2009 | Lin |
| 2010/0143481 A1* | 6/2010 | Shenoy ............. A61K 9/2077 424/489 |
| 2010/0260697 A1 | 10/2010 | Henry et al. |
| 2011/0082040 A1 | 4/2011 | Trevino et al. |
| 2012/0121743 A1 | 5/2012 | Garnier et al. |
| 2012/0251582 A1 | 10/2012 | Fortin |

FOREIGN PATENT DOCUMENTS

| EP | 826372 A2 | 3/2004 |
|---|---|---|
| RU | 2155062 C1 | 8/2000 |
| RU | 2314117 C1 | 1/2008 |
| RU | 2368388 C1 | 9/2009 |
| RU | 2401122 C1 | 10/2010 |

OTHER PUBLICATIONS

Caichampoo et al (Phytotherapy Research, 2009, vol. 23, pp. 289-292) (see abstract and introduction).*
Huang et al (Journal of Liquid Chromatography & Related Technologies, 2005, vol. 28, pp. 2383-2390, abstract).*

* cited by examiner

*Primary Examiner* — Mark V Stevens
(74) *Attorney, Agent, or Firm* — Fitch Even Tabin & Flannery LLP

(57) ABSTRACT

A composition comprising a standardized amount of a schisandrin compound and methods for production thereof for use in reducing stress, increasing blood antioxidant level, reducing lipid peroxidation and/or improving symptoms of depression in subjects in need thereof.

18 Claims, 18 Drawing Sheets

A)

B)

US 9,662,367 B2

ADAPTOGENIC COMPOSITIONS AND METHOD FOR PRODUCTION THEREOF

RELATED APPLICATIONS

This application claims the benefit of 35 USC 119 based on the priority of U.S. Provisional Application No. 62/032,307 filed Aug. 1, 2014, which is herein incorporated by reference.

FIELD

The disclosure relates to a composition such as a herbal composition or pharmaceutical composition comprising a standardized amount of a schisandrin compound and methods for production thereof for providing an adaptogenic and tonic effect in subjects in need thereof.

BACKGROUND

Among adaptogenic plants *Schisandra chinensis* (*Schisandra chinensis* (Turcz) Baill) has demonstrated an adaptogenic and tonic effect. In traditional Chinese medicine *Schisandra chinensis* has been used for at least 15 centuries. As a medicinal plant it has been described in Ben Cao Chang Mu (Compendium of Materia Medica) in 1596 written by the Chinese scientist Li Shi Zhen.

*Schisandra chinensis* is widely used in traditional medicine in many countries. In China, Japan and Tibet it is used as a tonic and stomachic agent. In Korea it has gained recognition as a tonic agent for improving general weakness, fatigue, sexual disorders. In traditional medicine of the peoples of Southeast Asia *Schisandra chinensis* is used to treat dysentery, gonorrhea, acute respiratory infections, pertussis, etc.

It has been shown that orally administered *Schisandra chinensis* fruits and seeds increase physical performance, promote endurance by individuals subjected to fatigue, remove sleepiness and sharpen visual function.

The biological activity of *Schisandra chinensis* seeds is due mainly to lignans (group phenylpropanoids), among which schisandrin (schisandrol A) is the most abundant.

The use of *Schisandra chinensis* fruits and seeds and their extracts in some formulations of food supplements is known. The majority of these complex preparations contain a number of components that are biologically active. However, *Schisandra chinensis* extracts occur in small amount therefore schisandrin content in preparations is either insignificant or not quantified.

The existing *Schisandra chinensis* preparations are available as alcoholic tinctures and are used in the form of drops. Such preparations are analyzed for ether oil content, the total amount of fat and ether oils and citric acid which is not a leading group of biologically active compounds of the plant in terms of interpretation of the tonic effect. Furthermore, the use of this dosage form does not provide accurate dosing, does not exclude the possibility of overdosing, does not provide the ease of taking the preparation, as well as its storage stability. The presence of alcohol in the preparation limits its use in some cases.

Fructus schisandrae has been described in U.S. 2009/0169653 which discloses a composition for prophylaxis of treatment of urinary system infection. U.S. Pat. No. 5,770,207 describes dietary supplements containing Kava root extract, Passion flower, *Chamomile* flowers, Hops and *Schisandra* fruit. U.S. 2012/0121743 describes a *Schisandra sphenanthera* fruit extract and cosmetic, dermatological and neutraceutical compositions.

SUMMARY

An aspect of the disclosure is a *Schisandra chinensis* seed oil extract comprising a schisandrin compound, wherein the *Schisandra chinensis* extract comprises at least 4% schisandrin compound.

Another aspect includes a composition, optionally a herbal composition, dietary supplement or pharmaceutical composition comprising a standardized amount of a schisandrin compound, optionally obtained from a *Schisandra chinensis* seed oil extract, and at least one or more excipients, wherein the standardized amount is from about 1 mg to about 10 mg per dosage unit.

In an embodiment, the composition is a solid dosage form.

In another embodiment, the one or more excipient comprising a filler, an adsorbent, a disintegrant and/or a glidant.

In an embodiment, the composition comprises an adsorbent and the adsorbent is magnesium aluminometasilicate (e.g. Neusilin® UFL2 or US2), magnesium carbonate, and/or mixtures thereof. In a particular embodiment, the absorbent is magnesium aluminometasilicate.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which.

DETAILED DESCRIPTION OF THE DISCLOSURE

I. Definitions

Figure 1:
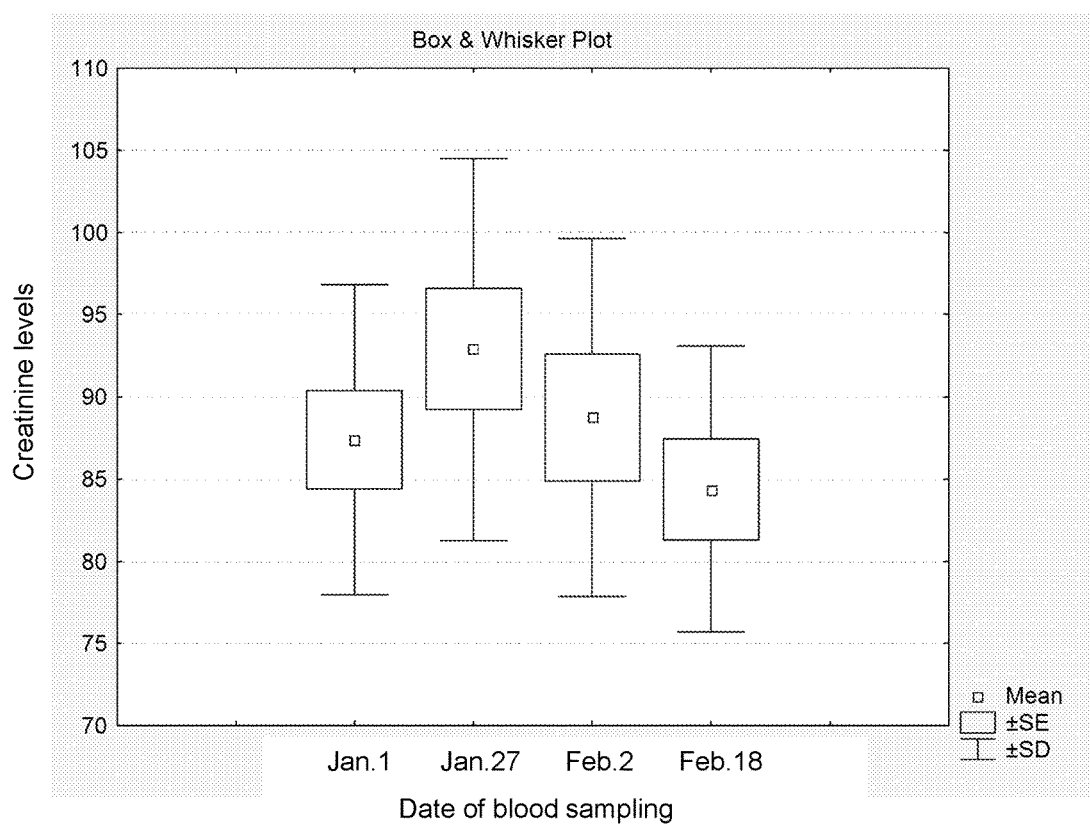
FIG. 1 is a Box & Whisker Plot of Creatinine levels.

The term "*Schisandra chinensis*", "*Schizandra chinensis*" or "wu-wei-zi" (in China) as used herein means a plant species from the Schisandraceae family known for its medicinal properties and used in traditional medicine in countries such as China, Korea, Japan and Russia. *Schisandra chinensis* has been described to possess adaptogenic properties and has a high content of dibenzocyclooctane lignans, including schisandrin, schisandrin A, schisandrol B, γ-schisandrin and gomisin A.

As used herein "schisandrin", "schizandrin", "schisandrol A" or "wuweizi alcohol A" means a compound found in *Schisandra chinensis* having the formula:

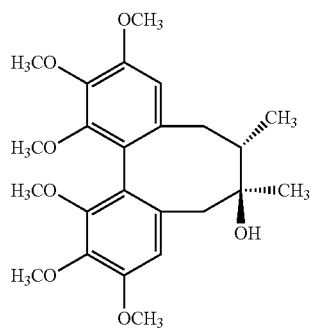 [SMILES: COc1cc2c(c(OC)c1OC)-c1c(cc(OC)c(OC)c1OC)C[C@](C)(O)[C@@H](C)C2]

or a salt or solvate thereof.

The term "adaptogenic and tonic effect" as used herein means an effect of stabilization of physiological processes and promotion of homeostasis. Examples of an adaptogenic and tonic effect are increased physical performance, increased endurance in individuals subjected to fatigue (e.g. as measured in the vertical swimming tests), decreased sleepiness, improved locomoter activity and emotional reactivity (e.g. as demonstrated in the Open field tests) increased brain activity and heightened visual function (e.g. as measured in the clinical studies). For example, it is known from the literature that frequent and short-time "grooming" is associated with a disturbance in grooming. Longer (in time) grooming on the contrary is associated with more comfortable behaviour. A high level of defecation further indicates the anxiety of the animal, its nervousness and fear. As shown below, the "open field" test marked a significant decrease in the number of acts of defecation in mice, suggesting a positive impact of *Schisandra* extract to reduce stress.

The term "subject" as used herein includes all members of the animal kingdom including vertebrates such as and including mammals such as and including but not limited to a primate such as human, monkey or ape, a dog, cat, cow, bull, buffalo, horse, goat, pig, rabbit, sheep, llama, camel, marsupial, a rodent such as a rat, or mouse, or a reptile, and suitably refers to a human.

As used herein, the term "dosage form" refers to the physical form of a dose for example comprising a compound of the disclosure, and includes without limitation liquid and solid dosage forms including, for example tablets, including enteric coated tablets, caplets, gelcaps, capsules, ingestible tablets, buccal tablets, troches, elixirs, suspensions, syrups, wafers, resuspendable powders, liquids, solutions as well as injectable dosage forms, including, for example, sterile solutions and sterile powders for reconstitution, and the like, that are suitably formulated for injection.

The term "filler" as used herein means an inactive substance in the pharmaceutical preparation of a solid dosage form used to fill out the size of a solid dosage such as a tablet or capsule in order to make practical the production and use.

The term "adsorbent" as used herein means an inactive substance capable of adsorption.

The term "disintegrant" as used herein means an inactive substance used in the pharmaceutical preparation of tablets which causes the tablets to dissolve on contact with moisture and release active ingredients for absorption.

The term "glidant" as used herein means an inactive substance used in the pharmaceutical formulation to reduce interparticle friction and cohesion.

The term "pharmaceutically acceptable" means compatible with the administration to or treatment of subjects, in particular humans.

The term "pharmaceutically acceptable salt" means an acid addition salt or a basic addition salt which is suitable for, or compatible with, the administration to or treatment of patients.

The term "pharmaceutically acceptable acid addition salt" as used herein means any non-toxic organic or inorganic salt of any basic compound. Basic compounds that form an acid addition salt include, for example, compounds comprising an amine group. Illustrative inorganic acids which form suitable salts include hydrochloric, hydrobromic, sulfuric and phosphoric acids, as well as metal salts such as sodium monohydrogen, orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art.

The term "pharmaceutically acceptable basic addition salt" as used herein means any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. The selection of the appropriate salt will be known to a person skilled in the art.

The formation of a desired compound salt is achieved using standard techniques. For example, the neutral compound is treated with an acid or base in a suitable solvent and the formed salt is isolated by filtration, extraction or any other suitable method.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

As used herein, the term "effective amount" or "therapeutically effective amount" means an amount effective, at dosages and for periods of time necessary to achieve the desired result. For example, the effective amount is an amount that reduces symptoms of stress, increases the blood antioxidant level, that reduces lipid peroxidation and that ameliorates symptoms of depression in a subject. Effective amounts may vary according to factors such as the disease state, age, sex, weight of the subject.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of addiction, stabilized (i.e. not worsening) state of addiction, delay or slowing of addiction progression, amelioration, diminishment of the reoccurrence of the addiction, and remission (whether partial or total), whether detectable or undetectable. "Treating" and "treatment" as used herein also include prophylactic treatment. The length of the treatment period depends on a variety of factors, the age of the patient, the concentration, the activity of the compounds described herein, and/or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required. For example, the compounds are administered to the subject in an amount and for a duration sufficient to treat the patient.

The term "mixture" as used herein, means a composition comprising two or more compounds. In an embodiment a mixture is a mixture of two or more distinct compounds. In a further embodiment, when a compound is referred to as a "mixture", this means that it can comprise two or more "forms" of the compounds, such as, salts, solvates, or, where applicable, stereoisomers of the compound in any ratio. A person of skill in the art would understand that a compound in a mixture can also exist as a mixture of forms. For example, a compound may exist as a hydrate of a salt. All forms of the compounds disclosed herein are within the scope of the present disclosure.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

Further, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

Further, it is to be understood that "a," "an," and "the" include plural referents unless the content clearly dictates otherwise. Thus for example, a composition containing "a compound" includes a mixture of two or more compounds.

It should also be noted that the term "or" is generally employed in its sense including "and/or" unless the content clearly dictates otherwise.

The term "about" means plus or minus 0.1 to 20%, 1-15%, or 1-10%, preferably up to 10% or up to 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. Section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

II. Compositions and Methods

Described herein is an economical method for preparing, standardizing, and/or preparing a composition, including a solid dosage form, of *Schisandra chinensis* seed oil extract comprising a standardized amount of schisandrin. Is it demonstrated herein that a standardized amount of a schisandrin compound obtained optionally from *Schisandra chinensis* seed and optionally extracted as a seed oil extract can provide for example an adaptogenic and tonic effect in a subject in need thereof.

Accordingly an aspect includes a *Schisandra chinensis* extract comprising a schisandrin compound, wherein the *Schisandra chinensis* extract comprises at least 4% schisandrin compound.

In an embodiment, the *Schisandra chinensis* extract comprises about or at least 4.1%, about or at least 4.2%, about or at least 4.3% about or at least 4.4%, about or at least 4.5%, about or at least 4.6%, about or at least 4.7%, about or at least 4.8%, about or at least 4.9% or about or at least 5.0% schisandrin compound.

If the *Schisandra chinensis* extract is a liquid, the amount of schisandrin compound in the extract can be weight per weight. As described, herein the amount of schisandrin compound can be standardized using a HPLC method described herein.

In another embodiment, the *Schisandra chinensis* extract comprises a seed oil extract. In a specific embodiment, the *Schisandra chinensis* extract is essentially a seed oil extract.

Several parts of the *Schisandra chinensis* plant can be used to obtain a *Schisandra chinensis* extract. For example, leaves, flowers, stems, roots, fruits, or other parts, or combinations thereof can be used. In a further example, leaves, flowers, stems, roots, fruits, or other parts, in combination with seeds can be used. The seed of the *Schisandra chinensis* plant is preferably used to obtain the extract. In an embodiment, the *Schisandra chinensis* extract is a seed oil extract.

Several extraction methods can be used to obtain an oil extract of *Schisandra chinensis*. For example, solvent extraction using water or an aqueous alcohol solution or an alcohol such as ethanol, methanol, isopropanol, hexane, or other suitable solvent, preferably ethanol, can be used. Another oil extraction method that can be used is the cold press method. Supercritical extraction using liquefied carbon dioxide can also be used. In yet another example, the oil extract of *Schisandra chinensis* can be obtained by using a combination of these extraction methods.

The schisandrin compound can be isolated from the *Schisandra chinensis* oil. Alternatively, it can be obtained using chemical or biochemical synthesis.

The supercritical extraction method involves using carbon dioxide in a supercritical state (e.g. liquefied carbon dioxide) as a solvent. This is an advantage over other extraction methods as carbon dioxide is non-toxic and more environmentally-friendly. Another advantage of the supercritical extraction method is that it leaves less residual solvent behind, allowing for a purer *Schisandra chinensis* extract. For example, no residual amounts of solvent in the extract were detected using the method described in the Examples, for example when extending beyond the supercritical pressure from 100 bar to 800 bar and using termperatures from about 30° C. to about 100° C. A combination of extraction methods can also be used.

In an embodiment, the *Schisandra chinensis* seed oil extract is obtained using a method comprising liquefied carbon dioxide at a supercritical pressure of about 100 bar to about 800 bar. In another embodiment, the supercritical pressure is about 200 bar to about 550 bar. In another specific embodiment, the supercritical pressure is about 300 bar to about 450 bar. In another embodiment, the pressure is about 350 to about 400 bar.

In a further embodiment, the seed oil is extracted using liquefied carbon dioxide at a temperature of about 30 to about 100 degrees Celsius. For example, the temperature is about 40 to about 80 degrees Celsius, about 45 to about 75 degrees Celsius, about 50 to about 70 degrees Celsius, or is about 55 to about 65 degrees Celsius.

In an embodiment, the seed oil extract is purified following extraction for removal of ballast substances.

In yet another embodiment, the amount of schisandrin compound in the *Schisandra chinensis* extract is standardized using high performance liquid chromatography.

The amount of schisandrin compound can be standardized using a high performance liquid chromatography (HPLC) method using for example chromatographic conditions described in Example 1. The HPLC method can be used to quantify the amount of schisandrin compound in the seed oil extract The sample preparation and extraction are for example optimized for schisandrin. In an example, the mobile phase can comprise a gradient of solvent A and solvent B, wherein solvent A comprises water and phosphoric acid and wherein solvent B comprises acetonitrile and phosphoric acid. The composition to be standardized is in an embodiment a *Schisandra chinensis* seed oil extract which was prepared as described in Example 1 using liquefied carbon dioxide at supercritical pressure.

It is also demonstrated herein that the composition prepared according to a method described herein is storage stable. For example, the schisandrin compound prepared as described in Example 1 remained stable and unchanged for six months under the following storage conditions: 40 degrees Celsius and 75% relative humidity, twelve months under the 30 degrees Celsius and 65% relative humidity, and 24 months under the 25 degrees Celsius and 60% relative humidity. Other studies conducted using the formulation tested in Example 1 have shown that the schisandrin compound is stable for at least or about one year.

In another embodiment, the schisandrin compound prepared as described in Example 1 can be stored at 25±2 degrees Celsius with relative humidity of 60±5% for 24 months without varying by more than 10% e.g. in terms of concentration.

Another aspect of the disclosure relates to a composition comprising a standardized schisandrin compound, and at least one or more excipients, wherein the standardized amount is from about 1 mg to about 10 mg per dosage unit.

In yet another embodiment, the standardized schisandrin comprised in the composition is comprises in a *Schisandra chinensis* seed oil extract.

In an embodiment, the composition comprises a standardized amount of schisandrin compound, for example in an amount from about 1 mg to about 10 mg per dosage unit, from about 2 mg to about 8 mg per dosage unit, from about 3 mg to about 5 mg per dosage unit, or is about 1 mg, about 2 mg, about 3 mg, about 4 mg, about 5 mg, about 6 mg, about 7 mg, about 8 mg, about 9 mg, or about 10 mg per dosage unit.

In an embodiment, the composition is a herbal composition. In another embodiment, the composition is a dietary supplement.

In an embodiment the dietary supplement, for prolonged use. In an embodiment, the dietary supplement comprises a standardized amount of schisandrin compound, the amount being from about 0.5 mg to about 5 mg per dosage unit, from about 1 mg to about 5 mg per dosage unit, from about 2 mg to about 5 mg per dosage unit, or is about 0.5 mg, about 1 mg, about 2 mg, about 3 mg, about 4 mg or about 5 mg.

In another embodiment, the composition is a pharmaceutical composition. Pharmaceutical compositions include, without limitation, lyophilized powders and suspensions. Other components that are optionally present in such compositions include, for example, water, surfactants, alcohols, polyols, glycerin and vegetable oils.

In an embodiment, the disclosure describes a composition wherein the dosage form is a solid dosage form. A solid dosage form includes individually coated tablets, capsules (including a soft capsule), granules or other non-liquid dosage forms suitable for oral administration. It is to be understood that the solid dosage form includes, but is not limited to, modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions can be formulated, e.g. liposomes or those wherein the active compound is protected with differentially degradable coatings, such as by microencapsulation, multiple coatings, etc. It is also possible to freeze-dry the compounds described herein and use the lyophilizates obtained, for example, for the preparation of products for injection.

If the *Schisandra chinensis* extract is comprised in a solid dosage form, the amount of schisandrin compound in the dosage form can be weight/weight.

In another embodiment, the composition is a soft capsule.

In an embodiment, the composition described herein is formulated for oral administration. Wherein the route of administration is oral, the dosage form may be, for example, incorporated with excipient and used in the form of enteric coated tablets, caplets, gelcaps, capsules, ingestible tablets, buccal tablets, troches, elixirs, suspensions, syrups, wafers, and the like.

In another embodiment, the disclosure describes a composition comprising one or more excipients. In a further embodiment, the one or more excipient comprises a filler, an adsorbent, a disintegrant and/or a glidant.

For example, the filler can comprise about 30% to about 95% of the pharmaceutical composition, the adsorbent can comprise about 2% to about 40% of the pharmaceutical composition by weight, the disintegrant can comprise about 0% to about 20% of the pharmaceutical composition by weight, and the glidant can comprise about 0% to about 10% of the pharmaceutical composition by weight (e.g. weight/weight).

Other components that can be comprised in the composition are for example carriers, diluents, solvents, preservatives, additives, antioxidants, electrolytes and pH control agents.

In an embodiment, the filler comprises lactose, microcrystalline cellulose, sorbitol, magnesium carbonate, calcium carbonate, calcium phosphate dibasic, and/or mixtures thereof.

In an embodiment, the adsorbent is magnesium aluminometasilicate (e.g. Neusilin® UFL2 or US2), magnesium carbonate, and/or mixtures thereof.

In an embodiment, the adsorbent is magnesium aluminometasilicate (Neusilin® UFL2 or US2).

In an embodiment, the disintegrant comprises low-substituted hydroxypropyl cellulose (L-HPC), polyvinylpolypyrrolidone (aslo known as crospovidone), potato starch, sodium starch glycolate, wheat starch, maize starch, rice starch, sodium carboxymethylcellulose calcium carboxymethylcellulose, and/or mixtures thereof.

In an embodiment, the glidant comprises talc, fumed silica (Aerosil®), starch, magnesium stearate, polyethylene glycol (PEG), for example PEG-4000, PEG-6000, and/or mixtures of any of the foregoing.

In an embodiment, the standardized amount of schisandrin compound, salt or solvate thereof is from about 1 mg to about 10 mg per dosage unit, from about 2 mg to about 8 mg per dosage unit, from about 3 mg to about 5 mg per dosage unit, or is about 1 mg, about 2 mg, about 3 mg, about 4 mg, about 5 mg, about 6 mg, about 7 mg, about 8 mg, about 9 mg, or about 10 mg per dosage unit.

In a further embodiment, each dosage unit comprises about or at least 1 mg, about or at least 2 mg, about or at least 3 mg, about or at least 4 mg, about or at least 5 mg, about or at least 6 mg, about or at least 7 mg, about or at least 8 mg, about or at least 9 mg, or about 10 mg of schisandrin compound, salt or solvate thereof. It will be evident to those skilled in the art that the number and frequency of administration will be dependent upon the response of the subject.

A further aspect provides a method of preparing a composition, comprising the steps:
a. obtaining a standardized amount of a schisandrin compound optionally by preparing a *Schisandra chinensis* seed oil extract and standardizing the amount of a schisandrin compound, for example as described herein;
b. mixing the standardized amount of the schisandrin compound, optionally the standardized seed oil extract, with an adsorbent to obtain a homogenous distribution;
c. adding one or more additional excipients to the mixture comprising the schisandrin compound and the adsorbent; and
d. compounding the excipient-mixture into a unit dosage form.

In an embodiment, the standardized amount of schisandrin compound is about 1 mg to about 10 mg per dosage unit.

In another embodiment, the *Schisandra chinensis* extract used in the method for preparing the pharmaceutical composition comprises a seed oil extract. In another embodiment, the *Schisandra chinensis* extract is a seed oil extract.

In yet another embodiment, high performance liquid chromatography is used to standardize the amount of schisandrin compound used in preparing the composition.

In a further embodiment, liquefied carbon dioxide at supercritical pressure of about 100 to about 800 bar and a temperature of about 30 to about 100 degrees Celsius is used to obtain the *Schisandra chinensis* seed oil extract used in preparing the formulation. In yet a further embodiment, the supercritical pressure is about 200 to about 550 bar and the temperature is about 40 to about 80 degrees Celsius. In another specific embodiment, the supercritical pressure is about 300 bar to about 450 bar. In another embodiment, the pressure is about 350 to about 400 bar. For example, the temperature is about 45 to about 75 degrees Celsius, about 50 to about 70 degrees Celsius, or is about 55 to about 65 degrees Celsius.

In an embodiment, the composition is prepared as a solid dosage form. In another embodiment, the composition prepared as a soft capsule.

In yet another embodiment, the composition is formulated for oral administration.

In preparing the compositions, the one or more excipients can be one or more fillers, additional adsorbents, disintegrants and/or glidants.

In an embodiment, the filler comprises lactose, microcrystalline cellulose, sorbitol, magnesium carbonate, calcium carbonate, calcium phosphate dibasic, and/or mixtures thereof.

In an embodiment, the adsorbent (e.g. in the composition, added to the seed oil extract or the additional adsorbent) is magnesium aluminometasilicate (Neusilin® UFL2 or US2), magnesium carbonate, and/or mixtures thereof.

In an embodiment, the adsorbent is magnesium aluminometasilicate (Neusilin® UFL2 or US2), In an embodiment, the disintegrant comprises and/or is selected from the group consisting of low-substituted hydroxypropyl cellulose (L-HPC), polyvinylpolypyrrolidone (aslo known as crospovidone), potato starch, sodium starch glycolate, wheat starch, maize starch, rice starch, sodium carboxymethylcellulose calcium carboxymethylcellulose, and mixtures thereof.

In an embodiment, the glidant comprises talc, fumed silica (Aerosil®), starch, magnesium stearate, polyethylene glycol(PEG), and/or mixtures thereof. In an embodiment the PEG is PEG-000, or PEG 6000.

In a further embodiment, each prepared dosage unit comprises about or at least 1 mg, about or at least 2 mg, about or at least 3 mg, about or at least 4 mg, about or at least 5 mg, about or at least 6 mg, about or at least 7 mg, about or at least 8 mg, about or at least 9 mg, or about 10 mg of schisandrin compound, salt or solvate thereof. The number and frequency of administration can be dependent for example upon the response of the subject.

Methods described herein allow for compounding of smaller dosage forms which can be less difficult to administer than larger solid dosage forms.

A further aspect is a method for providing an adaptogenic and tonic effect in a subject in need thereof comprising administering to the subject a composition comprising a standardized amount of a schisandrin compound, salt or solvate thereof.

Yet another aspect discloses use of a composition comprising a standardized amount of a schisandrin compound, salt or solvate thereof for providing an adaptogenic and tonic effect.

In another embodiment, the disclosure describes an adaptogenic and tonic effect of a composition comprising a standardized amount of a schisandrin compound. For example, as shown herein administration of the composition to a subject can increase antioxidant activity, reduce lipid peroxidation, improve symptoms of depression, decrease stress, increase physical activity, decrease blood glucose level, and decrease bilirubin level.

In an embodiment, the composition comprising a standardized amount of a schisandrin compound is administered daily. In another embodiment, the composition is administered twice daily. In yet another embodiment, it is administered every two days. In another embodiment, the composition comprising a standardized amount of a schisandrin compound, salt or solvate thereof is administered for about 10 to about 30 days. It will be evident to those skilled in the duration of administration will be dependent upon the response of the subject.

As demonstrated in the Examples, beneficial effects are manifested during the time of taking the standardized schisandrin composition.

In an embodiment, administration of the composition comprising a standardized amount of a schisandrin compound is repeated, optionally over several days. As demonstrated herein, experiments were conducted in mice to study the effect of a schisandrin compound on the level of physical activity and of stress. Multiple administration of an amount of a schisandrin compound can be more effective than single administration.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1 Quantification of a Schisandrin Compound Using High Performance Liquid Chromatography

*Schisandra chinensis* is used in Russia in the form of a tincture 1:5 with an ethanol percentage of 95%. It is prescribed to patients to improve symptoms of fatigue, exhaustion and excessive drowsiness. The tincture is produced in an alcohol-based solution and is administered as drops. However, such administration does not provide precise dosage, does not prevent overdose, is not convenient to administer and does not provide storage stability. Also, the presence of alcohol in this formulation reduces its usage.

The analysis of the *Schisandra* seed tincture drug is conducted by analyzing the content of essential oil, the sum of fatty and essential oils, and citric acid that are not biologically active compounds of *Schisandra chinensis* which provide a tonic effect. The fruits and seeds of *Schisandra chinensis* as well as its extracts are also known to be used as dietary supplements. Schisandrin is present in small amounts hard or impossible to determine.

A high performance liquid chromatography (HPLC) method was developed to quantitate the schisandrin compound contained in the *Schisandra chinensis* extract. Schisandrin (≥98%) obtained from Sigma-Aldrich was used as a control. The content of the schisandrin compound in the *Schisandra chinensis* seed oil extracts ranged from about 4.2 to 4.9% depending on the extraction for example, prior to standardization.

Schisandrin extract has been obtained by *Schisandra chinensis* seed extraction with liquefied carbon dioxide at supercritical pressure 200-550 bar and a temperature of 40-80° C.

A High-performance liquid chromatography method has been developed to quantify the schisandrin in the extract:
Mobile Phase:
  Solvent A: Water—P-0, 1 n solution of phosphoric acid (99/1, v/v);
  Solvent B: Acetonitrile P-0, 1 n solution of phosphoric acid (99/1, v/v)
Gradient:
  0-28 min, 60% solvent A, 40% Solvent B;
  28-38 min, 40% solvent A, 60% Solvent B;
  38-45 min, 60% solvent A, 40% Solvent B.

Preparation of 0.1 N phosphoric acid solution: 8.7 ml of phosphoric acid P is added in a volumetric flask of 1000.0 ml. The solution volume is adjusted to the mark and thoroughly mixed.

Preparation of the working standard sample of Schisandrin: 10.0 mg of the standard sample of Schisandrin (Sigma, SML0054-50 mg) is placed into a volumetric flask 10.0 ml, dissolved in methanol P. The volume of solution is adjusted to the mark with the same solvent and stirred. 1.0 ml of the resulting solution is transferred into a 10.0 ml volumetric flask. The volume of the solution is adjusted to the mark with the same solvent. The concentration is 0.1 mg/ml.

Preparation of test solution: 60.0 mg *Schisandra chinensis* extract is placed in a 25.0 ml volumetric flask, is dissolved in a mixture of water and methanol (1:1 ratio), then adjusted to the mark with the same solvent. The resulting solution is filtered through the PVDF filter with pore diameter of 0.45 microns, while removing the first portion of filtrate. The concentration is adjusted to 0.1 mg/ml.

Chromatographic Conditions:
Column: Agilent Zorbax Eclipse XDB-C 18, 150 mm length and 4.6 mm internal diameter filled with octadecylsilyl silica gel, 5 micron particle size;
Flow rate: 1 ml/min;
Detection at wavelength: 250 nm;
Volume of injection sample: 10 µl;
Column temperature: 25° C.

The quantitated amount of schisandrin remained stable and unchanged for six months under the following storage conditions: 40 degrees Celsius and 75% relative humidity, 12 months under the 30 degrees Celsius and 65% relative humidity, and 24 months under the 25 degrees Celsius and 60% relative humidity.

Pre-Clinial Studies

Research comparing the properties of *Schisandra chinensis* seed tincture (solution 1) and *Schisandra chinensis* seed oil extracted using liquefied carbon dioxide at supercritical pressure (solution 2), more specifically comparing the effect on behavioral activity, physical performance and lipid peroxidation of blood in white mice showed the following:

1. Administration of solution 1 and solution 2 led to an increase in physical performance under stress, increase in the level of activity and decrease in emotionality. Similar results were demonstrated using less dosage of solution 2;
2. Solution 2 showed sign of possible cumulative effect;
3. Solution 2 demonstrated superior antioxidant activity.

Conclusions drawn from the laboratory, pre-clinical studies, showed that the *Schisandra chinensis* seed oil (Solution 2) that was extracted using liquefied carbon dioxide at supercritical pressure can be used as a component in a drug with an adaptogenic and tonic effect.

Example 2: Assessment of Performance in the Test "Vertical Swimming" in Mice

Nonlinear white mice (males) were used in the studies, reproduced in the vivarium VSMU (stock is delivered by the nursery "Rappolovo" (Russian Federation)). Before the test animals were kept for 2 weeks in quarantine conditions at 18-20 degrees Celsius, 60-70% humidity and natural photoperiod. The animals were kept in accordance with the standards of group or individual placement in the natural photoperiod; they received a standard diet and drinking water in sufficient quantity. The test and control groups were randomly formed by body weight as the leading feature. The animals weighing 36-38 g at the age of 3 to 4 months were selected. Each group consisted of 10 mice.

The test and control solutions were administered orally to the animals: the solution at doses 1, 2, 3—once; the solution at dose 2—three times spaced by an interval of 24 hours, the control—once and three times spaced by an interval of 24 hours, in a volume of 0.3 ml/head using syringes with metering accuracy of 0.01-0.02 ml and intragastric olive-net probes. Dose 1 contained the least amount of the Schisandrin compound, and dose 3 contained the greatest amount of the Schisandrin compound.

After 16 hours following the last administration of the test solution in the test and control animals working capacity was assessed. The test reflects the state of depression and represents a hard kind of stress which combines physical and emotional stress. During the test, all animals—test groups, control and intact, were subjected to stress—swimming in the pool with the load. The pool is a metal container (thermostatic water bath). The water level is not less than 30 cm, the water temperature is maintained around 26 degrees Celsius±0.5 degrees Celsius. The animals swim with a load (consisting of metal clips attached to the root of the tail) equal to 5% of body weight. They swim to full fatigue, as evidenced by the dipping of the animal in the bottom of the pool. The swimming duration is estimated by the difference between the start of swimming and the full immersion of the animal in the water.

Statistical Analysis

The statistical processing of the results was performed using the software package Statistica 6.0 (StatSoft Inc, USA), Excell. The mean value of the studied parameters, the standard error (m), 95% confidence intervals were determined in the test group (M). Taking into consideration the small sample and the misdistribution of the studied parameters, the significance of sample differences was assessed by the non-parametric analysis for U-criterion of Wilcoxon-Mann-Whitney test. The differences were considered significant at p 0.05.

Results

The results of test solutions action compared with the placebo and the intact group at single and triple oral administration are presented tables 1 to 3.

TABLE 1

Effect of the test solutions on the physical endurance of male mice after a single dose in the test "vertical swimming" (n = 10) compared with the intact group and the controls [1]

| Groups, solutions, doses (ml/head) | Time schedule | Swimming duration (min) |
|---|---|---|
| Group 13 (intact) | | 34.4 ± 13.79 |
| | Test solution | |
| Group 11 placebo (control) | 16 hours | 30.3 ± 9.1 |
| Group 5, solution - dose 1 | 16 hours | 66.5 ± 24.8 |
| Group 6, solution - dose 2 | 16 hours | 81.7 ± 23.9 * |
| Group 7, solution - dose 3 | 16 hours | 57.2 ± 17.9 |

Note:
* statistically significant differences in the U- criterion of Mann-Whitney test: group 6 compared with the intact group (p < 0.05);
[1] the effect of the test solution was compared with the intact group and the control (Group 11)

TABLE 2

Results of the comparative effect of the test solutions at various doses on physical endurance of male mice after single injection in the "Vertical swimming" test

| Groups, solutions, doses (ml/head) | Time schedule Test solution | Swimming duration (min) |
|---|---|---|
| Group 5, solution- dose 1 | 16 hours | 66.5 ± 24.8 |
| Group 6, solution - dose 2 | 16 hours | 81.7 ± 23.9 * |
| Group 7, solution - dose 3 | 16 hours | 57.2 ± 17.9 |

Note:
* statistically significant differences in the U- criterion of Mann -Whitney test The studies of the influence of extracts on the swimming duration in the "vertical swimming" test showed that when administered at dose 2 (group 6) the swimming duration increased significantly compared with the intact animals (group 13) (Table 1). The comparison of the swimming duration with the group of control (group 11 placebo) animals revealed no significant differences. The lower average and/or lack of statistical effect of the extract at dose 3 may indicate a non-linear dependence on the dose of the substance.

TABLE 3

Effect of the test solutions on the physical endurance of male mice after a triple dose in the "Vertical swimming" test (n = 10) compared with the intact group and the control [1]

| Groups, solutions, doses (ml/head) | Time schedule | Swimming duration (min) |
|---|---|---|
| Group 13 (intact) | | 34.4 ± 13.79 |
| Group 12 placebo (control) | 64 hours | 39.2 ± 18.59 |
| Group 8, solution - dose 2 | 64 hours | 92.5 ± 15.57 * |

Note:
* statistically significant differences in the U- criterion of Mann -Whitney test: group 8 compared with the intact group and the control (group 12).
[1] group 8 was compared with the intact group and the control (group 12)

Each injection was spaced by an interval of 24 hours. The studies were conducted 16 hours after the last injection. By the triple administration of the extract at dose 2 the significant increase in swimming was revealed (group 8). The extract injection resulted in the significant increase in the swimming duration compared with both the intact group (group 13) and control group (group 12 placebo).

Considering the existence of differences between the control solution and the extract administration (dose 2), high efficiency and direct influence on the duration of the swimming is suggested. Taking into account the differences identified at a single dose, the presence of positive cumulative effect in the extract is suggested, too. Thus, the following conclusions are made:

1. The extract was the most effective at dose 2, which includes multiple administration.
2. The extract may have dose-related cumulative efficiency.

Example 3: Evaluation of Behavioral Activity in Mice

Nonlinear white mice (males) were used in the studies, reproduced in the vivarium VSMU (stock is delivered by the nursery "Rappolovo" (Russian Federation)). Before the test animals were kept for 2 weeks in quarantine conditions at 18-20 C, 60-70% humidity and natural photoperiod. The animals were kept in accordance with the standards of group or individual placement in the natural photoperiod; they received a standard diet and drinking water in sufficient quantity. The test and control groups were randomly formed by body weight as the leading feature. The animals weighing 36-38 g at the age of 3-4 months were selected. Each group consisted of 10 individuals.

The test and control solutions were administered orally to the animals: the solution at doses 1,2,3—once; the solution at dose 2—three times, the control—once and three times, in a volume of 0.3 ml/head using syringes with metering accuracy of 0.01-0.02 ml and intragastric olive-net probes.

The monitoring of behavioral activity of the animals was carried out after 16 hours following the last administration of the extract. In the test "open field" a potentially dangerous situation is simulated by placing the animals in the chamber, which is much more than the cell in which they live. The testing was conducted at constant artificial light, at the same time for 3 minutes using toxicological equipment PANLAB (Spain), equipped with video surveillance and recording of animal behavior, followed by data processing using the computer program SMART (Spain).

For the peripheral visual sector the following parameters were recorded: Number of stances (regarded as an index of research activity); Number of grooming acts (treated as "mixed" behavior); Number of defecations (autonomic function);

By using the software SMART the video was analyzed, the position of the animal was determined in the arena, which allows recording the following parameters: Total distance (in cm); Movement time, Immobility time, Average speed (cm/sec); Latent period of withdrawal from the center.

The animals with less physical activity and more bowel movements in the test "open field" are regarded as more emotional (stressed) than those who move a lot and have little defecation.

Statistical Analysis

The statistical processing of the results was performed using the software package Statistica 6.0 (StatSoft Inc, USA), Excell. The mean value of the studied parameters, the standard error (m), 95% confidence intervals were determined in the test group (M). Taking into consideration the small sample and the misdistribution of the studied parameters, the significance of sample differences was assessed by the non-parametric analysis for U-criterion of Wilcoxon-Mann-Whitney test. The differences were considered significant at p 0.05.

Results

The effects of test and control solutions on locomotor activity and emotional reactivity parameters of male mice by the single and triple administration are shown in Tables 4.

TABLE 4

Effect of test solutions and controls on locomotor activity and parameters of emotional reactivity in male mice in the "open field" at single injection (n = 10) compared with the intact and control groups [1]

| Groups solutions, doses (ml/head) | Time schedule | Activity | | Number of acts | |
|---|---|---|---|---|---|
| | | Total distance (cm) | VMA (stances) | grooming | defecation |
| Group 13 (intact) | | 1374.65 ± 171.25 | 9.9 ± 3.69 | 2.0 ± 0.26 | 3.9 ± 0.74 |
| | | Test solution | | | |
| Group 11 placebo (solution-control) | 16 hours | 1990.0 ± 146.7 | 14.7 ± 2.03 | 1.5 ± 0.5 | 2.4 ± 0.5 |
| Group 5, solution-dose 1 | 16 hours | 1361.0 ± 88.36* | 11.56 ± 2.48 | 1.0 ± 0.01 | 3.5 ± 0.4 |
| Group 6, solution-dose 2 | 16 hours | 1419.7 ± 226.74* | 19.7 ± 3.2 | 1.2 ± 0.2 | 2.87 ± 0.58 |

TABLE 4-continued

Effect of test solutions and controls on locomotor activity and parameters of emotional reactivity in male mice in the "open field" at single injection (n = 10) compared with the intact and control groups [1]

| Groups solutions, doses (ml/head) | Time schedule | Activity Total distance (cm) | VMA (stances) | Number of acts grooming | defecation |
|---|---|---|---|---|---|
| Group 7, solution-dose 3 | 16 hours | 1217 ± 58.7* | 9.9 ± 2.2 | 1.0 ± 0.01 | 2.7 ± 0.6 |

Note:
*statistically significant differences in the U- criterion of Mann -Whitney test: group 5, 6, 7 compared with the control (p ≤ 0.05).

The analysis of stress effect of placebo showed that the injection of reference solutions led to significant growth (compared with the intact animals) of the distance of mice in placebo groups. Thus, preliminary stressing of animals by the placebo solution leads to some increase in behavioral activity.

The administration of the preparation leveled the effect, making the distance mice similar to the characteristic of the intact group. The solution, like in the studies of the swimming duration, showed its positive effect on the VMA (vertical motor activity) at dose 2 compared with the intact group and group 7.

TABLE 5

Effect of the triple administration of the test solution on motor activity and emotional activity parameters of mice in the test "open field"

| Groups solutions, doses (ml/head) | Time schedule | Activity Total distance (cm) | VMA (stances) | Number of acts grooming | defecation |
|---|---|---|---|---|---|
| Group 13 (intact) | | 1374.65 ± 171.25 | 9.9 ± 3.69 | 2.0 ± 0.26 | 3.9 ± 0.74 |
| Group 12 placebo (control) | 72 hours | 1542 ± 90.12 | 11 ± 2.73 | 1.0 ± 0.01 | 2.5 ± 0.17 |
| Group 8, solution-dose 2 | 72 hours | 1723.8 ± 180.28 | 13.1 ± 2.58 | 1.0 ± 0.01 | 1.7 ± 0.28* |

Note:
*statistically significant differences in the U- criterion of Mann -Whitney test compared with the intact group, (p ≤ 0.05).

By the triple injection of dose 2 the solution had a positive effect on the stress levels of animals, causing a decrease in the number of defecation acts.

TABLE 6

Comparative analysis of the test solution effect on locomotor activity and parameters of emotional activity of male mice in the test "open field" after the single and triple administration (n = 10)

| Groups solutions, doses (ml/head) | Time schedule | Activity Total distance (cm) Test solution | VMA (stances) | Number of acts grooming | defecation |
|---|---|---|---|---|---|
| Group 6 solution dose 2 | 16 hours | 1419.7 ± 226.74 | 19.7 ± 3.2 | 1.2 ± 0.2 | 2.87 ± 0.58 |
| Group 8, solution-dose 2 | 72 hours | 1723.8* ± 180.28 | 13.1 ± 2.58 | 1.0 ± 0.01 | 1.7 ± 0.28 |

Note:
*statistically significant differences in the U- criterion of Mann -Whitney test compared with groups 6 and 8, (p ≤ 0.05).

When comparing the behavioral responses of mice after the single (group 6) and triple (group 8) administration of test solutions the index of locomotor activity was significantly higher in group 8 in comparison to the same solution and the same dose administered once (group 6).

TABLE 7

Comparative analysis of the control effect on locomotor activity and parameters of emotional activity of male mice in the test "open field" after the single administration (n = 10)

| Groups solutions, doses (ml/head) | Time schedule | Activity Total distance (cm) | VMA (stances) | Number of acts grooming | defecation |
|---|---|---|---|---|---|
| Group 13 (intact) | | 1374.65 ± 171.25 | 9.9 ± 3.69 | 2.0 ± 0.26 | 3.9 ± 0.74 |
| Group 11 placebo (control) | 16 hours | 1990.0* ± 146.7 | 14.7* ± 2.03 | 1.5 ± 0.5 | 2.4 ± 0.5 |

Note:
*statistically significant differences in the U- criterion of Mann -Whitney test compared with the intact group.

When comparing the control (placebo) effect on mice, the significant increase in locomotor activity was observed in the control group compared with the intact one.

TABLE 8

Comparative analysis of the control effect on locomotor activity and parameters of emotional activity of male mice in the test "open field" after the triple administration (n = 10)

| Groups solutions, doses (ml/head) | Time schedule | Activity Total distance (cm) | VMA (stances) | Number of acts grooming | defecation |
|---|---|---|---|---|---|
| Group 13 (intact) | | 1374.65 ± 171.25 | 9.9 ± 3.69 | 2.0 ± 0.26 | 3.9 ± 0.74 |
| Group 12 placebo (control) | 72 hours | 1542 ± 90.12 | 11 ± 2.73 | 1.0 ± 0.01 | 2.5 ± 0.17 |

Table 8 shows that there is no significant difference between the control (placebo, group 12) and intact group (group 13) after the triple administration.

Conclusion

Assessing the behavior of the animals in the test "open field", the following conclusions are made:
1. After single administration and among doses 1 to 3, dose 2 was the most effective in terms of increasing physical activity and decreasing stress (as measured by the number of defecation acts)
2. After triple administration and among doses 1 to 3, dose 2 was the most effective in terms of increasing physical activity and decreasing stress (as measured by the number of defecation acts).
3. At similar dose (dose 2), triple administration was more effective than single administration in terms of physical activity and decreasing stress (as measured by the number of defecation acts).

Example 4: Method of Testing the Activity of Free Radical Oxidation and Blood Antioxidant Activity in Mice To investigate the activity of lipid peroxidation and antioxidant activity (AOA) of blood the test mice were decapitated after the test "open field" under ether anesthesia using a guillotine manufactured by PANLAV (Spain). The blood was taken into glass tubes and exposed in the refrigerator at +4° C. till clotting reaction.

The serum was obtained by centrifugation in the refrigerate centrifuge PC-6 at 1500 rev/min for 20 minutes.

The resulting serum was assayed by induced chemiluminescence method on the device biochemiluminometer BCL-06.

The method of chemiluminescence inducing by hydrogen peroxide ferrous sulfate is based on the catalytic decomposition of hydrogen peroxide with metal ions of variable valence.

Thus, the hydroxyl radicals formed in Fenton reaction act as initiators of free radical oxidation (FRO). As a result of the recombination of peroxide radical reaction, the molecular products are formed and quantum of light is released, which determines the observed chemiluminescence. The defined light sum (S) for 30 seconds (photon quantity) and the maximum light intensity.

The maximum intensity (Imax) depends on the content of FRO products in the sample. Waning occurs due to the reaction of the antioxidant system present in the sample. The complex of molecular entities possessing pro-oxidant and antioxidant action affects CL intensity.

Methods

For assessing FRO serum the most important indicators are:

Imax—the maximum intensity during the experiment, mV;

S—area under the intensity curve or total light sum;

tg2—tangent of maximum slope of the curve to the time axis;

The values Imax and S (total light sum) reflect the importance of lipid peroxidation. The value tg2 (negative value) reflects the antioxidant activity of blood serum.

Statistical Analysis

The statistical processing of the results was performed using the software package Statistica 6.0 (StatSoft Inc, USA), Excell. The mean value of the studied parameters, the standard error (m), 95% confidence intervals were determined in the test group (M). Taking into consideration the small sample and the misdistribution of the studied parameters, the significance of sample differences was assessed by the non-parametric analysis for U-criterion of Wilcoxon-Mann-Whitney test. The differences were considered significant at $p \leq 0.05$.

Results

The influence of the test and control samples extracts of *Schisandra* on the parameters of free radical processes of blood serum of mice after the test "open field" showed that the administration of the placebo caused negative changes in the investigated parameters. There was a significant increase in the activity of free radical oxidation (FRO). The single administration of *Schisandra* extract at dose 3 leveled the negative effects of the introduction of the reference solution, approaching the value of the investigated parameters to normal values of intact animals.

TABLE 9

Influence of solution at single dose on FRO parameters

| Groups, solutions, doses (ml/head) | Biochemiluminescence parameters | | |
|---|---|---|---|
| | Flash light sum (S), mV · c | Intensity of max. flash (Imax), mV | Tangent angle of kinetic curve incidence (tgα2) |
| Group 5, solution-dose 1 | 11.82 ± 1.2* | 1.13 ± 0.15* | 0.26 ± 0.04* |
| Group 6, solution-dose 2 | 12.00 ± 0.66* | 1.16 ± 0.09* | 0.25 ± 0.02* |
| Group 7, solution-dose 3 | 13.22 ± 0.75 | 1.35 ± 0.14* | 0.31 ± 0.04* |
| Group 11, control | 12.94 ± 1.00* | 1.32 ± 0.10 | 0.29 ± 0.03 |
| Group 13, intact | 11.71 ± 0.35 | 1.26 ± 0.07* | 0.31 ± 0.02* |

Note:
*significant differences from the control (p < 0.05). Significant differences are revealed between group 5 and groups 7, 11, 13; group 6 and groups 7, 11, 13; between group 11 (control) and intact animals.

The injection of the reference (placebo) solution has led to an increase of FRO activity. However, the increase concerned only general light sum. The single administration of all doses of the test solution had positive effect on FRO parameters, significantly increasing antioxidant activity and flash height at doses 1 and 2. Dose 3 had some negative pro-oxidant effect.

Thus, the extract was effective at doses 1 and 2.

TABLE 10

Influence of solution at single dose on FRO parameters

| Groups, solutions, doses (ml/head) | Biochemiluminescence parameters | | |
|---|---|---|---|
| | Flash light sum (S), mV · c | Intensity of max. flash (Imax), mV | Tangent angle of kinetic curve incidence (tgα2) |
| Group 8, solution-dose 2 | 12.82 ± 1.33 | 1.32 ± 0.21 | 0.29 ± 0.05 |
| Group 12, control | 12.60 ± 1.14 | 1.24 ± 0.15 | 0.29 ± 0.04 |
| Group 13, intact | 11.71 ± 0.35 | 1.26 ± 0.07 | 0.31 ± 0.02 |

Note:
*significant differences from the control (p < 0.05). No significant differences between the groups.

Thus, the multiple administration of the solution had no effect on FRO parameters.

Also, the comparative analysis between the groups of animals treated with solutions at various doses with intact animals has been carried out.

TABLE 11

Comparative characteristics of the action of the solution (dose 1) on FRO parameters

| Groups, solutions, doses (ml/head) | Biochemiluminescence parameters | | |
|---|---|---|---|
| | Flash light sum (S), mV · c | Intensity of max. flash (Imax), mV | Tangent angle of kinetic curve incidence (tgα2) |
| Group 5, solution-dose 1 | 11.82 ± 1.2* | 1.13 ± 0.15* | 0.26 ± 0.04* |
| Group 13, intact | 11.71 ± 0.35 | 1.26 ± 0.07 | 0.31 ± 0.02 |

Note:
*significant differences from the control (p < 0.05). Significant differences are revealed between group 6 and group 13

The solution at dose 1 doesn't negatively impact FRO parameters compared to intact animals.

TABLE 12

Comparative characteristics of the action of the solution (dose 2) on FRO parameters

| Groups, solutions, doses (ml/head) | Biochemiluminescence parameters | | |
|---|---|---|---|
| | Flash light sum (S), mV · c | Intensity of max. flash (Imax), mV | Tangent angle of kinetic curve incidence (tgα2) |
| Group 6, solution-dose 2 | 12.00 ± 0.66* | 1.16 ± 0.09* | 0.25 ± 0.02* |
| Group 13, intact | 11.71 ± 0.35 | 1.26 ± 0.07 | 0.31 ± 0.02 |

Note:
*significant differences from the control (p < 0.05).

At dose 2 the solution has a positive effect on FRO parameters by reducing the activity of lipid peroxidation (LPO) and increasing antioxidant activity (AOA). The increase of AOA is also marked in comparison with intact animals.

TABLE 13

Action of the solution (dose 3) on FRO parameters

| Groups, solutions, doses (ml/head) | Biochemiluminescence parameters | | |
|---|---|---|---|
| | Flash light sum (S), mV · c | Intensity of max. flash (Imax), mV | Tangent angle of kinetic curve incidence (tgα2) |
| Group 7, solution-dose 3 | 13.22 ± 0.75 | 1.35 ± 0.14 | 0.31 ± 0.04 |
| Group 13, intact | 11.71 ± 0.35 | 1.26 ± 0.07 | 0.31 ± 0.02 |

Note:
*significant differences from the control (p < 0.05). No significant differences between the groups.

Thus, the solution at dose 3 has no effect on the studied parameters.

TABLE 14

Action of the multiple injection of the solution (dose 2) on FRO parameters

| Groups, solutions, doses (ml/head) | Biochemiluminescence parameters | | |
|---|---|---|---|
| | Flash light sum (S), mV · c | Intensity of max. flash (Imax), mV | Tangent angle of kinetic curve incidence (tgα2) |
| Group 8, solution-dose 2 | 12.82 ± 1.33 | 1.32 ± 0.21 | 0.29 ± 0.05 |
| Group 13, intact | 11.71 ± 0.35 | 1.26 ± 0.07 | 0.31 ± 0.02 |

Note:
* significant differences from the control (p < 0.05). No significant differences between the groups.

Thus, the multiple injection of the solution at dose 2 has no effect on the studied parameters.

Conclusion

1. The single administration of the placebo solution has led only to the increase in the total light sum. 2. The single administration of the solution at doses 1 and 2 has leveled the negative effect of placebo. Dose 3 had some pro-oxidant effect. 3. The multiple administration of the solution at dose 2 had no effect on the studied FRO parameters. 4. The solution at dose 2 has increased AOA compared with intact animals.

General Conclusions of Pre-Clinical Studies

1. Physical endurance and working capacity: 1.1 The increase of physical performance of animals under hard stress upon the administration of the extract solution as compared with the control groups is observed. 1.2 The possibility of a dose-dependent cumulative effect of the extract solution is suggested.

2. Motor activity and emotionality: 2.1 The increased motor activity and decreased level of emotionality of animals upon the administration of the extract solution is observed. 2.2 The possible of dose-dependent cumulative effect of the extract solution is suggested.

3. Antioxidant activity: 3.1 The antioxidant activity of the extract solution is marked.

Example 5: Studies of the Brain Activity in Humans

Previous pre-clinical studies of mice with single and triple administration of Schisandrin determined that the most effective dose was dose 2. When extrapolated, dose 2 in mice corresponds to a dose of 4 mg for humans.

In accordance with the one aspect of the present patent using the obtained extract as the active substance with the fixed content of *Schisandra chinensis* main lignan—Schisandrin in amount of from 1 to 4 mg per dosage unit, the following pharmaceutical formulations have been developed:

1. The pharmaceutical formulation as a capsule comprising the *Schisandra chinensis* seed extract obtained by supercritical CO2-extraction and excipients.
2. The pharmaceutical formulation comprising the *Schisandra chinensis* seed extract obtained by supercritical CO2 extraction and excipients for producing a solid dosage form.

The formulation contains excipients (lactose, MCC, sorbitol), adsorbents (magnesium aluminometasilicate (Neusilin UFL2 or US2)), disintegrators (potato starch, sodium starch glycolate), glidants (talc, magnesium stearate, aerosil).

The pharmaceutical composition was formulated into a solid dosage form by mixing the active ingredient, the *Schisandra chinensis* seed extract, standardized for Schisandrin, with adsorbents until homogeneous distribution throughout the mass of the extract. The remaining excipients were added to the obtained mass. The mixture was mixed, dusted and finally, converted into a single dosage form.

The data on therapeutic efficacy of a pharmaceutical containing *Schisandra chinensis* extract standardized for schisandrin as an active ingredient are supported by the results of clinical studies.

Studies of brain activity were conducted on 10 volunteers using EEG (electroencephalography). The parameters were recorded using the instrument Neuron-Spectrum—5 (sampling rate—500 Hz, mounting—monopolar 16, highpass filter—0.5 Hz low-pass filter—35.0 Hz). The readings were taken in dynamics—before and after taking the drug at interval—1 hour (max—4 hours).

The increased brain activity was observed after 1 hour and remained for 4 hours after a single dose of the preparation containing 4 mg of the schisandrin compound per a dosage unit.

Example 5: Study of Visual Acuity and Functional State of the Retina in Humans

Study of visual acuity and the functional state of the retina were performed on 8 volunteers using ERG (electroretinography) (program ERG Standart, EP-1000, version 3.2.0). The uptake of the preparation was set as follows: 1 capsule containing 4 mg of the schisandrin compound per capsule, every day for 20 days. The readings were taken before the treatment, after 10 days of the treatment, after 20 days of the treatment and after 10 days after the cessation of the medication.

Visual acuity increased to some extent in 6 patients with different visual disorders after 10 days of taking the preparation; 3 patients had an improvement of cone ERG from moderate-depressed to normal.

Example 7: Biochemical Blood Studies

The experimental group of consisted 10 individuals (n=10) 17.01, 27.01 and 8 individuals (n=8) 07.02, 18.02. The individuals received 1 capsule containing 4 mg of the schisandrin compound per capsule, every day for 20 days. The readings were taken one day before the start of the treatment (17.01), after 10 days of the treatment (27.01), after 20 days of the treatment (7.02) and after 10 days after the cessation of the medication (18.02). The table shows the means and standard deviations for each parameter in the format M±s for each period, as well as, the achieved significance level p is specified when comparing dependent groups (compared with the control). For the comparison of the groups the paired two-sample t-test for means was used.

TABLE 15

Means and standard deviations of biochemical parameters

Figure 2:
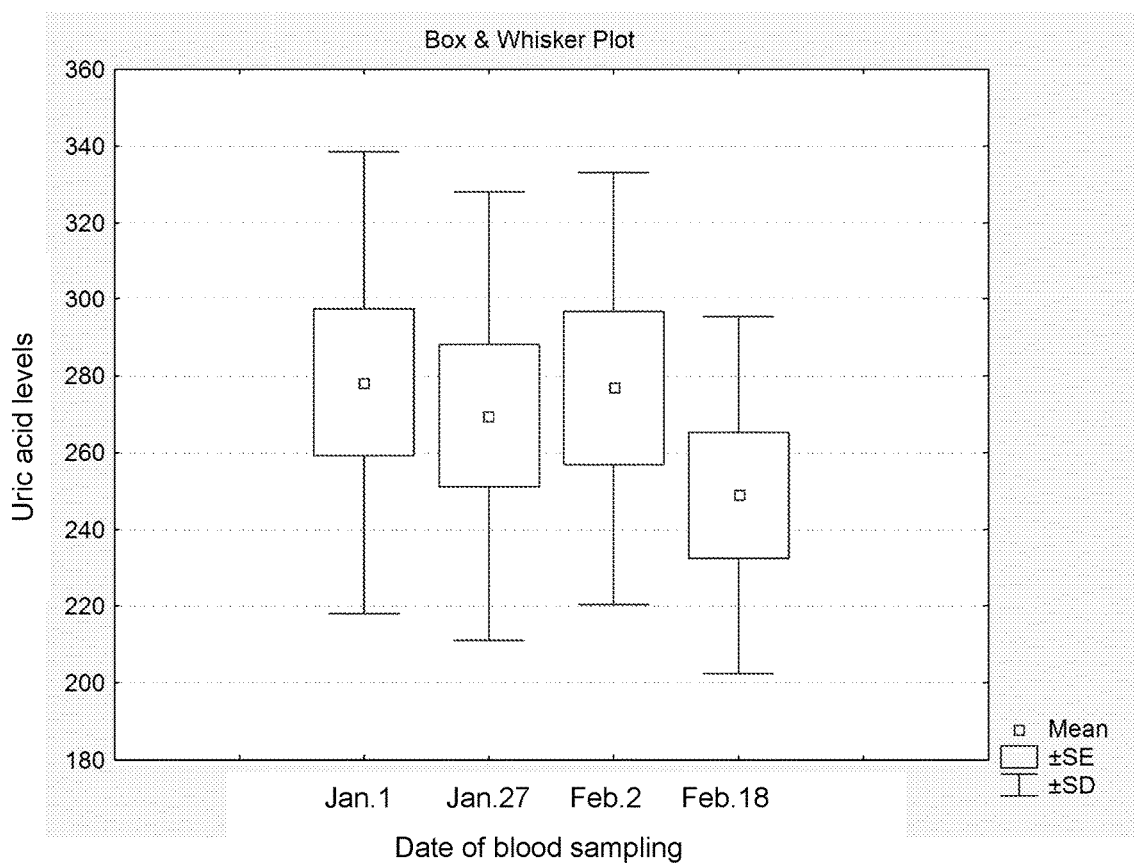
FIG. 2 is a Box & Whisker Plot of Uric acid levels.
Figure 3:
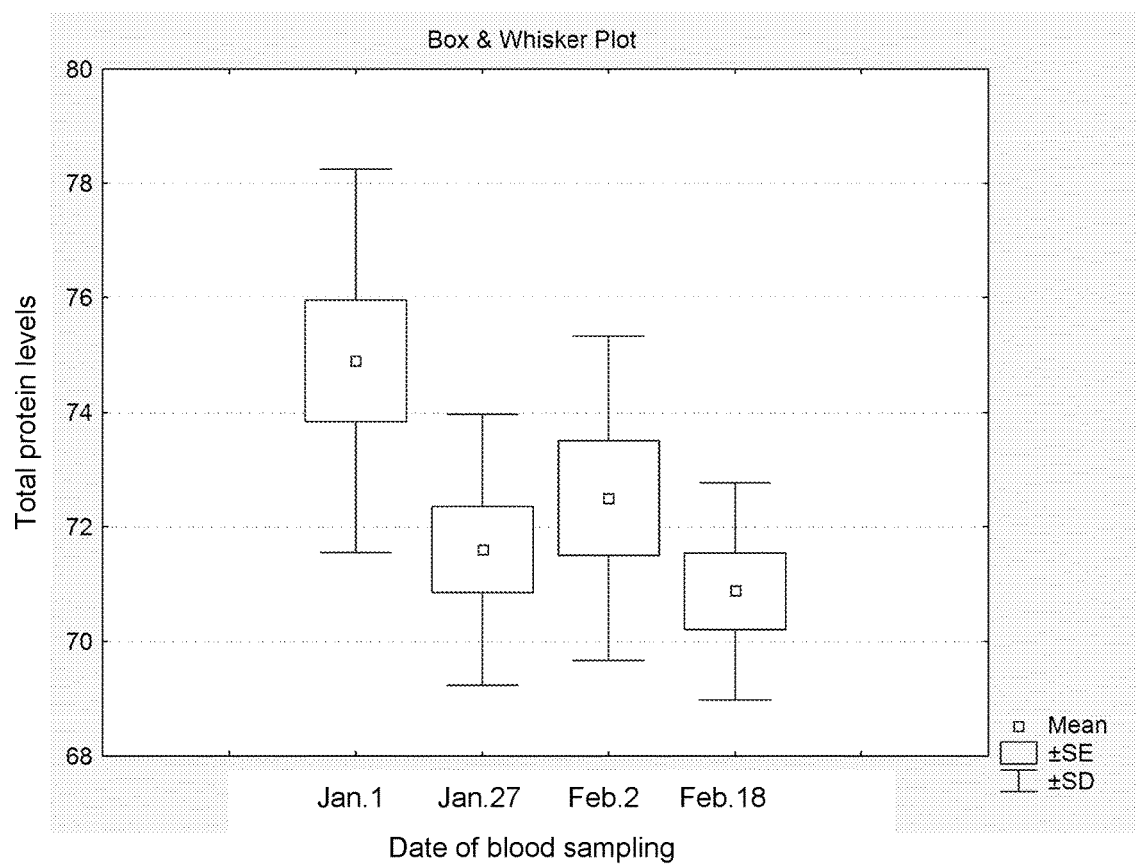
FIG. 3 is a Box & Whisker Plot of Total protein levels.
Figure 4:
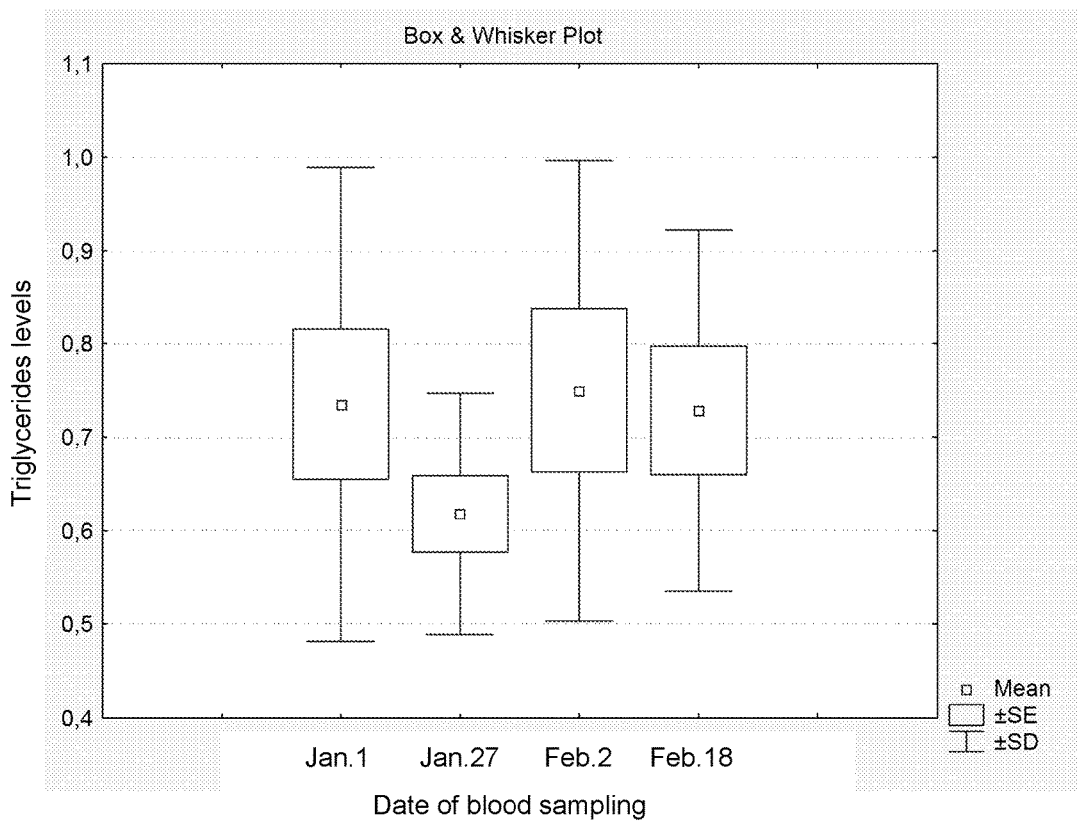
FIG. 4 is a Box & Whisker Plot of Triglyceride levels
Figure 5:
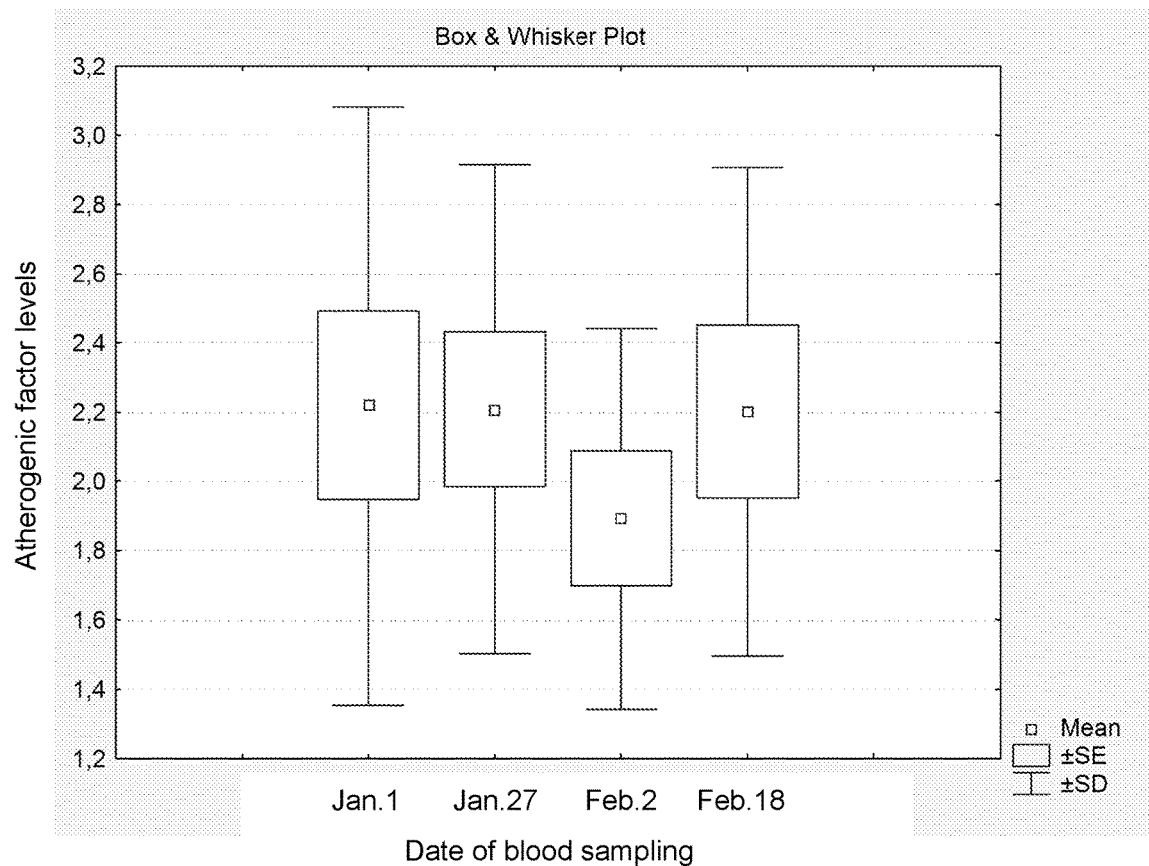
FIG. 5 is a Box & Whisker Plot of Calcium levels
Figure 6:
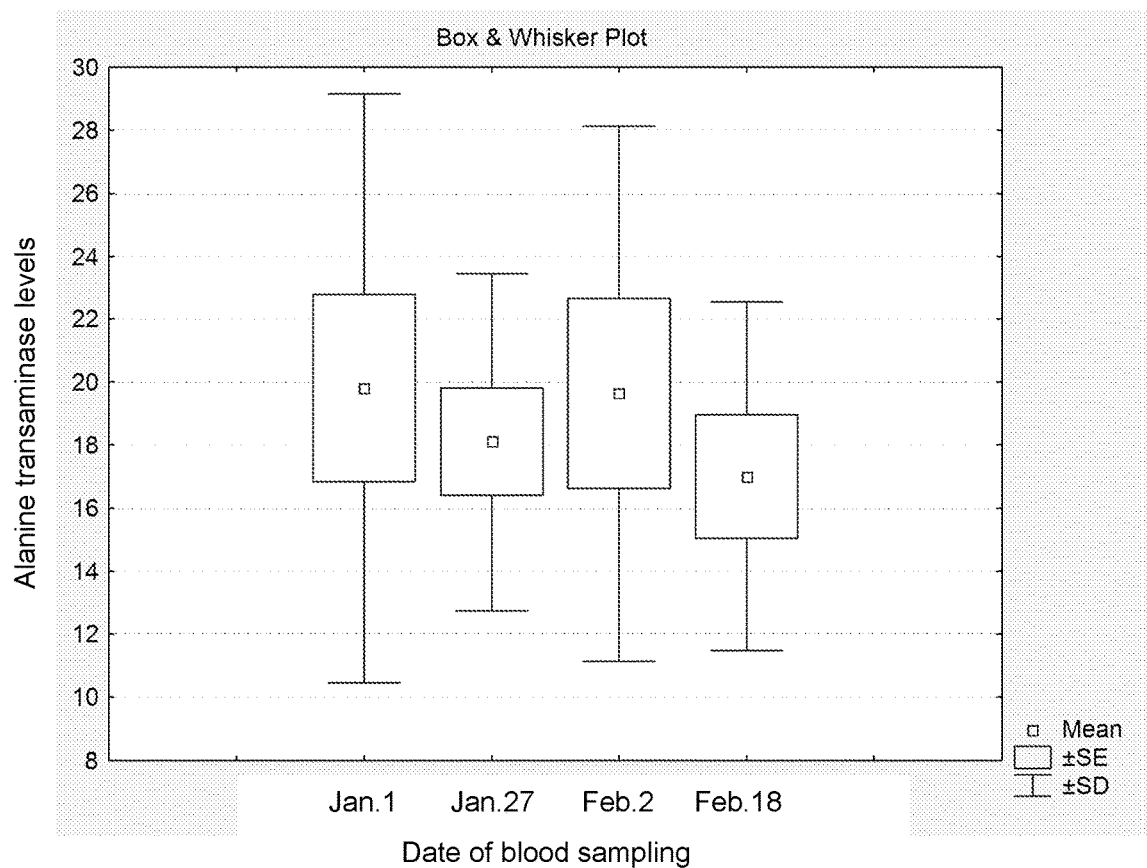
FIG. 6 is a Box & Whisker Plot of Alanine transaminase levels
Figure 7:
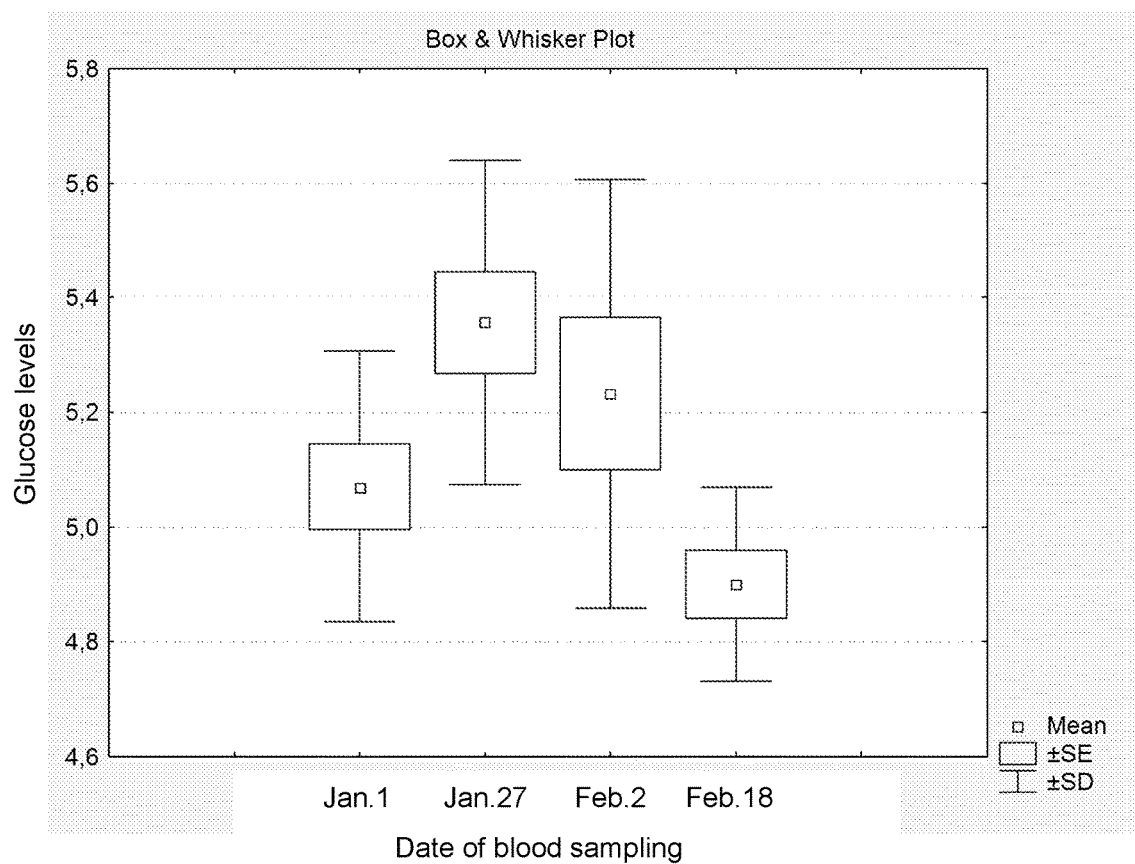
FIG. 7 is a Box & Whisker Plot of Glucose levels
Figure 8:
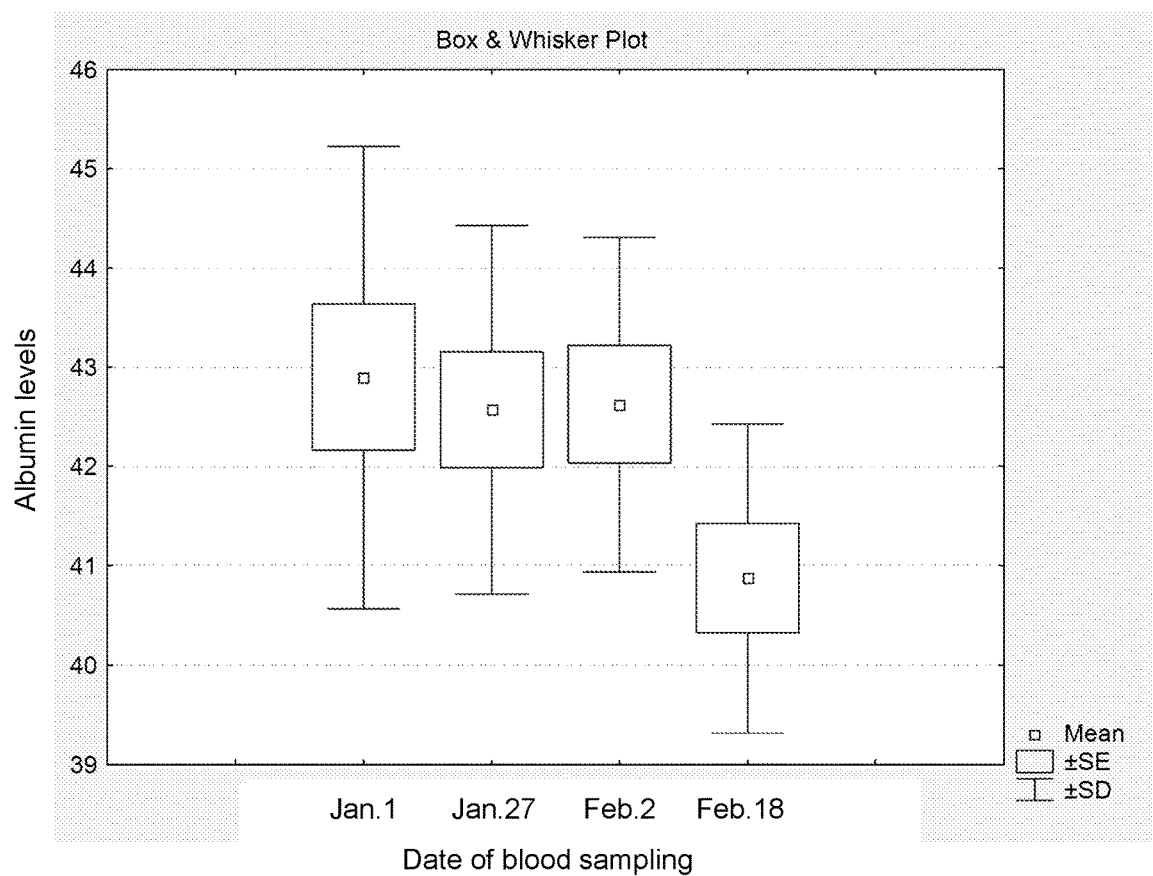
FIG. 8 is a Box & Whisker Plot of Albumin levels
Figure 9:
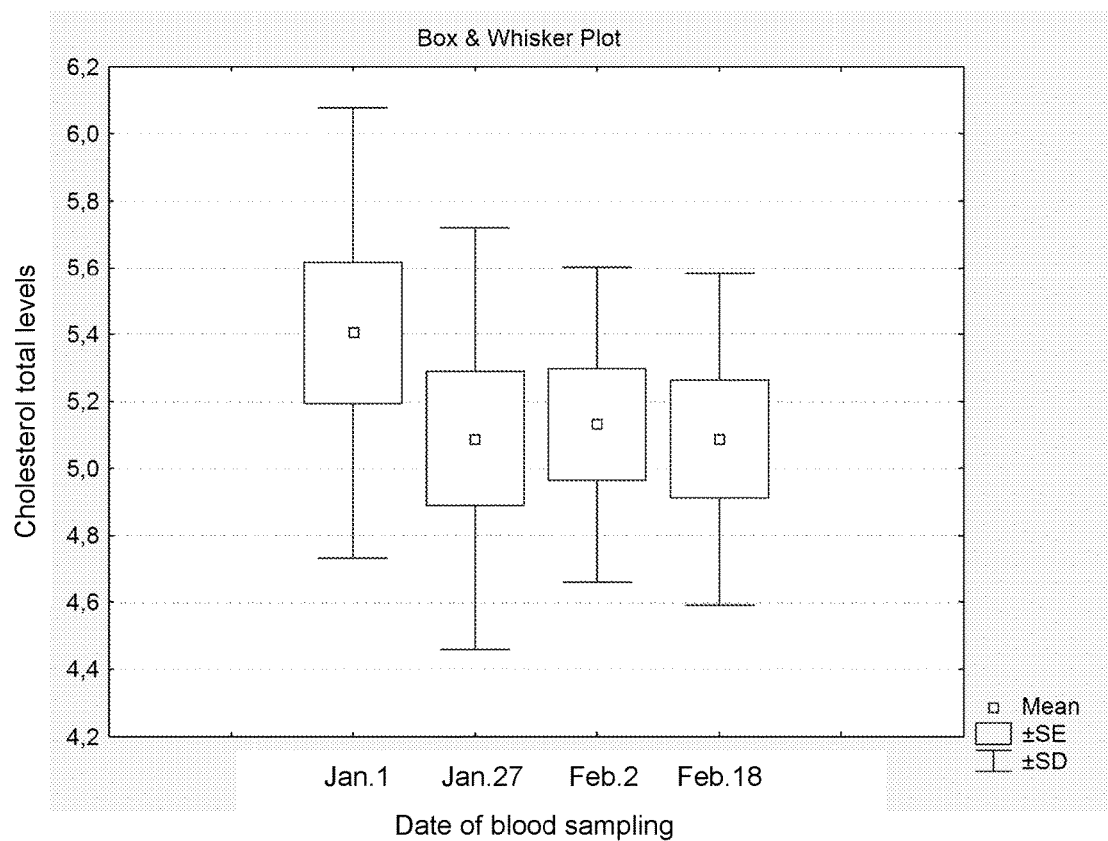
FIG. 9 is a Box & Whisker Plot of Total cholesterol levels
Figure 10:
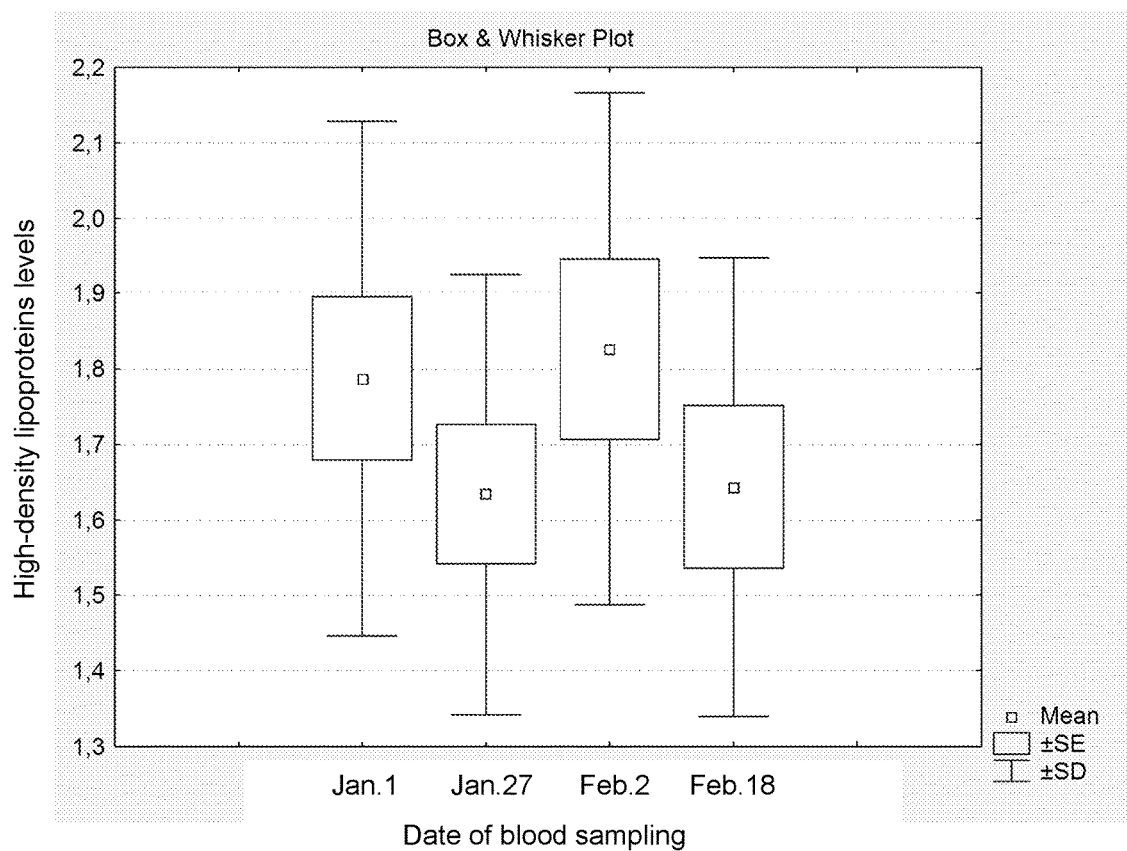
FIG. 10 is a Box & Whisker Plot of High density lipoprotein levels
Figure 11:
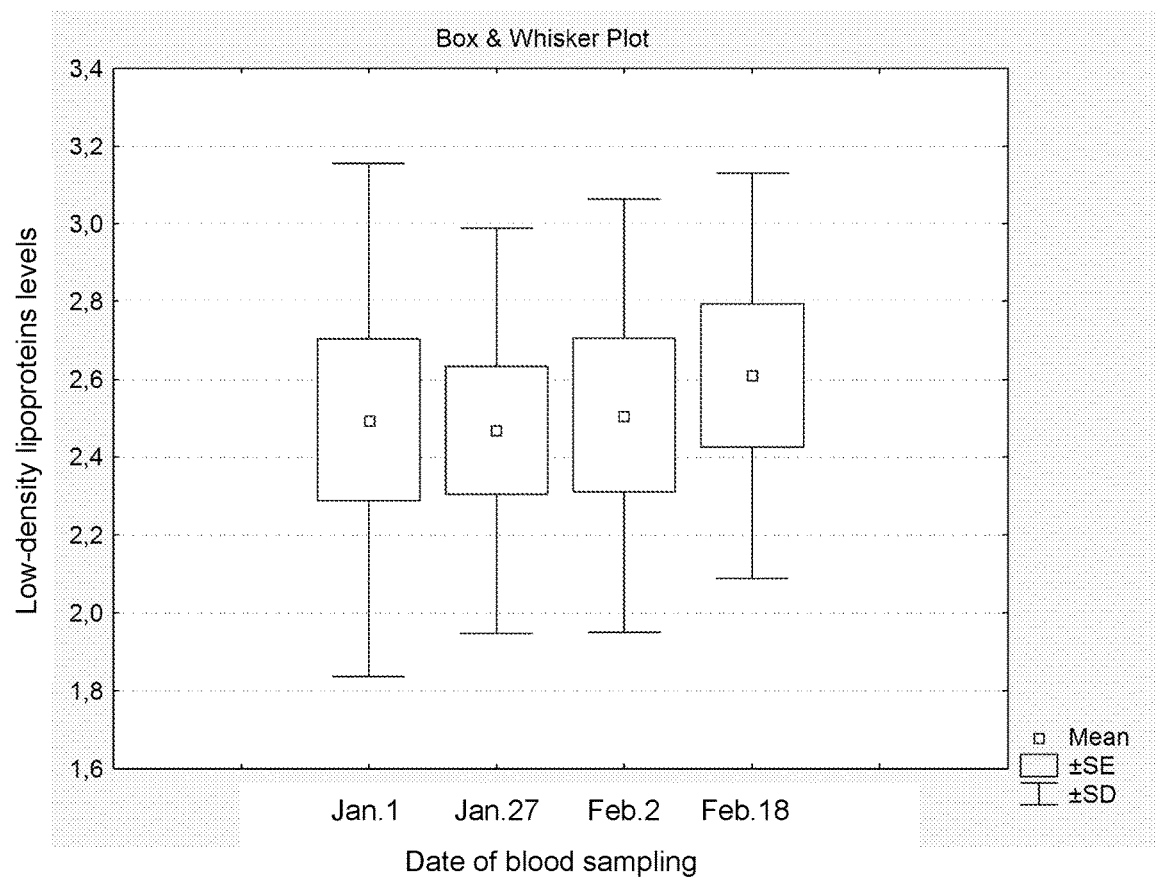
FIG. 11 is a Box & Whisker Plot of Low density lipoprotein levels
Figure 12:
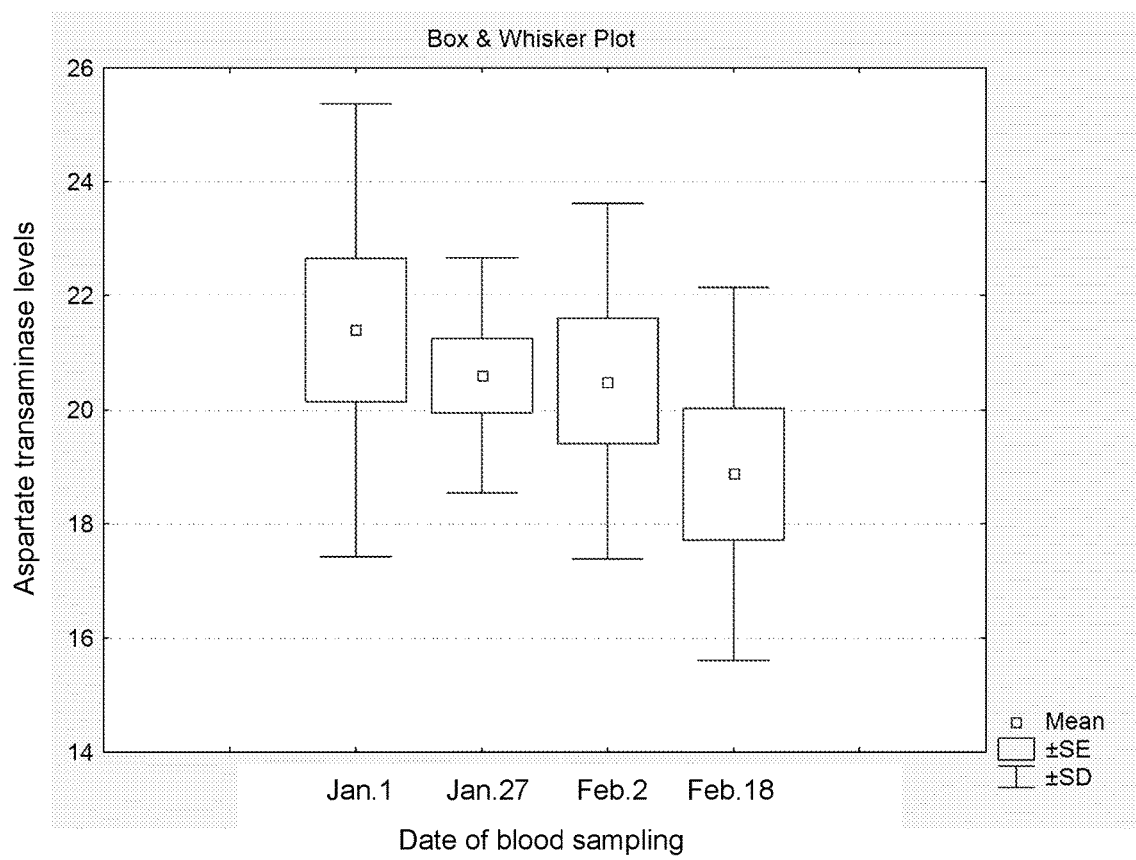
FIG. 12 is a Box & Whisker Plot of Aspartate aminotransferase levels
Figure 13:
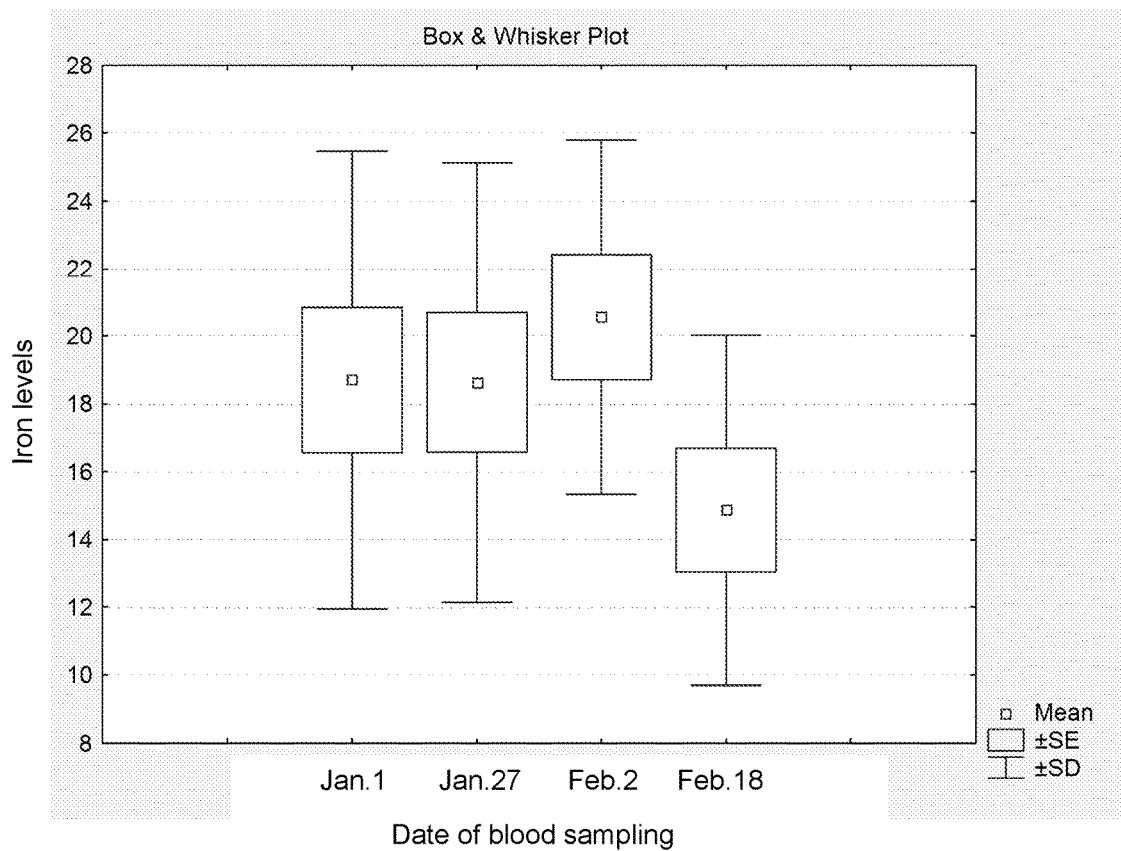
FIG. 13 is a Box & Whisker Plot of Iron levels
Figure 14:
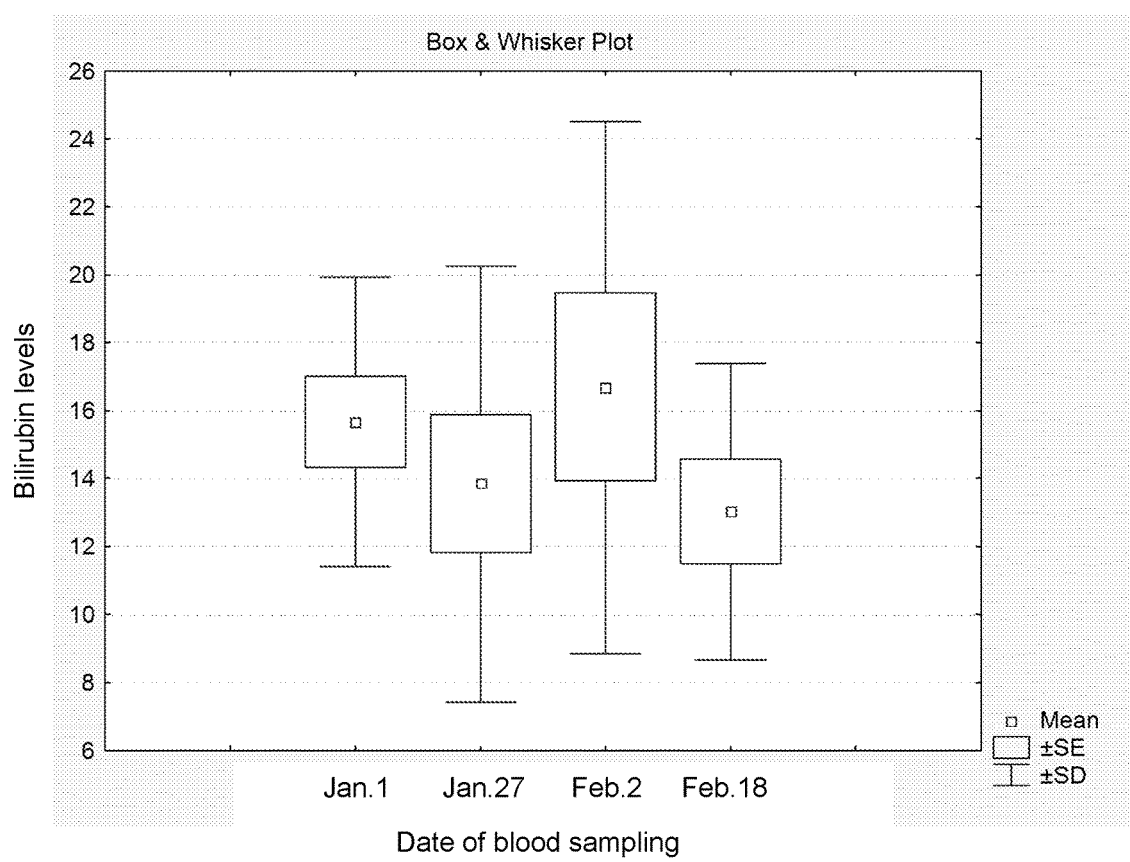
FIG. 14 is a Box & Whisker Plot of Total bilirubin levels
Figure 15:
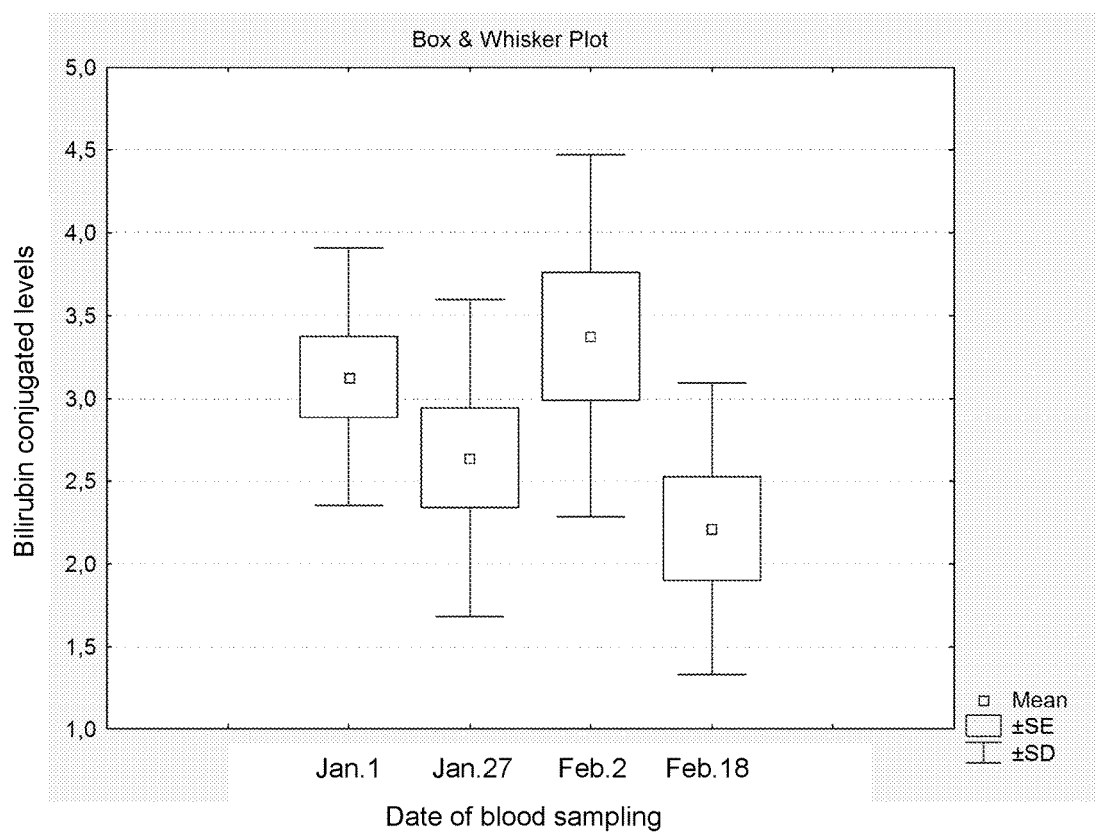
FIG. 15 is a Box & Whisker Plot of Direct bilirubin levels
Figure 16:
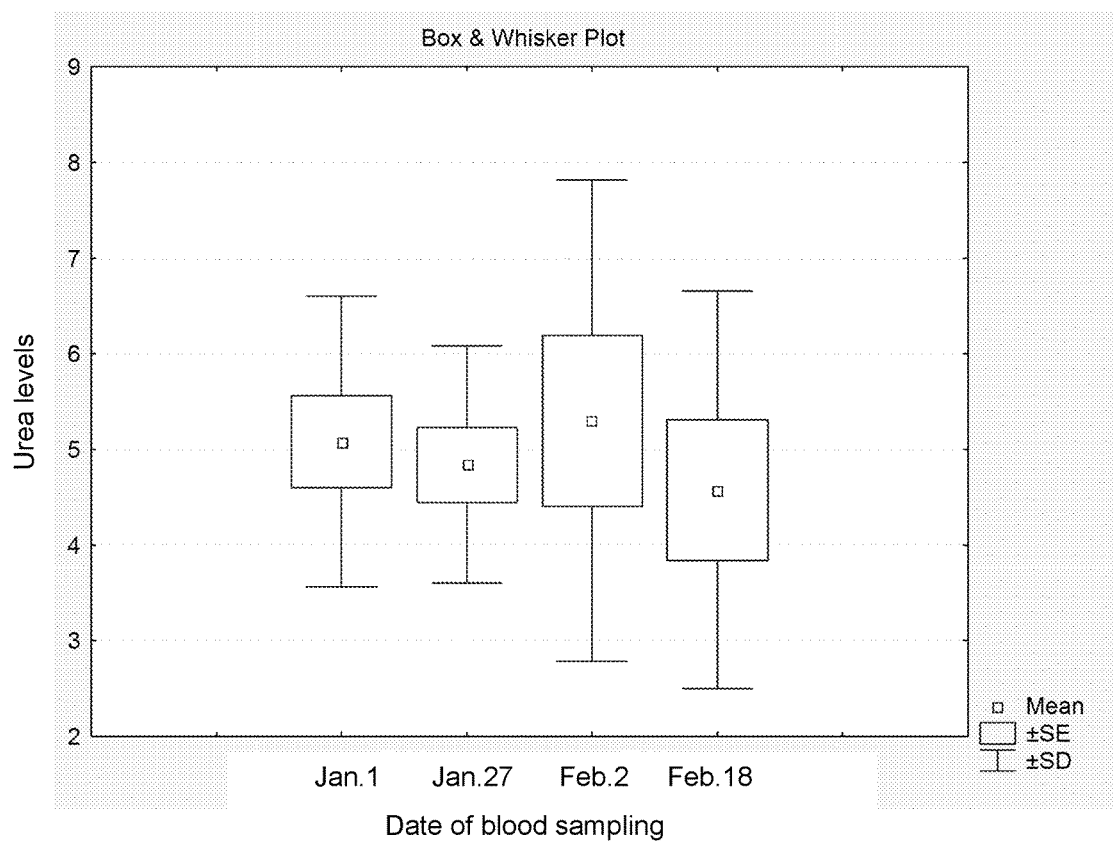
FIG. 16 is a Box & Whisker Plot of Urea levels

| Parameter | 17.01 (n = 10) | 27.01 (n = 10) | 07.02 (n = 8) | 18.02 (n = 8) |
|---|---|---|---|---|
| Glucose (FIG. 7) | 5.07 ± 0.24 | 5.36 ± 0.28** | 5.23 ± 0.37 | 4.9 ± 0.17** |
| Urea (FIG. 16) | 5.08 ± 1.52 | 4.84 ± 1.24 | 5.3 ± 2.52 | 4.58 ± 2.08* |
| Creatinine (FIG. 1) | 87.4 ± 9.45 | 92.9 ± 11.62* | 88.75 ± 10.9 | 84.38 ± 8.7 |
| Total bilirubin (FIG. 14) | 15.66 ± 4.26 | 13.85 ± 6.41 | 16.69 ± 7.83 | 13.03 ± 4.35** |
| Direct bilirubin (FIG. 15) | 3.13 ± 0.78 | 2.64 ± 0.96 | 3.38 ± 1.09 | 2.21 ± 0.88** |
| Uric acid (FIG. 2) | 278.3 ± 60.33 | 269.6 ± 58.52 | 276.75 ± 56.4 | 248.88 ± 46.53 |
| Total protein (FIG. 3) | 74.9 ± 3.35 | 71.6 ± 2.37*** | 72.5 ± 2.83 | 70.88 ± 1.89*** |
| Albumin (FIG. 8) | 42.9 ± 2.33 | 42.57 ± 1.86 | 42.63 ± 1.69 | 40.88 ± 1.55** |
| Total cholesterol (FIG. 9) | 5.41 ± 0.67 | 5.09 ± 0.63** | 5.13 ± 0.47 | 5.09 ± 0.5 |
| High density lipoprotein (FIG. 10) | 1.79 ± 0.34 | 1.63 ± 0.29** | 1.83 ± 0.34 | 1.64 ± 0.3*** |
| Low density lipoprotein (FIG. 11) | 2.5 ± 0.66 | 2.47 ± 0.52 | 2.51 ± 0.56 | 2.61 ± 0.52 |
| Triglycerid (FIG. 4) | 0.74 ± 0.25 | 0.62 ± 0.13 | 0.75 ± 0.25 | 0.73 ± 0.19 |
| Calcium (FIG. 5) | 2.22 ± 0.86 | 2.21 ± 0.71 | 1.89 ± 0.55 | 2.2 ± 0.7 |
| Alanine transaminase (FIG. 6) | 19.8 ± 9.35 | 18.1 ± 5.36 | 19.63 ± 8.5 | 17 ± 5.53 |
| Aspartate aminotransferase (FIG. 12) | 21.4 ± 3.98 | 20.6 ± 2.07 | 20.5 ± 3.12 | 18.88 ± 3.27* |
| Iron (FIG. 13) | 18.7 ± 6.77 | 18.63 ± 6.49 | 20.56 ± 5.23 | 14.86 ± 5.15 |

Note:
*$p < 0,1$;
**$p < 0.05$;
***$p < 0.01$

FIGS. 1 to 16 show Mean, Standard error of Mean, Standard deviation for each parameter.

Example 8: Chromatogram of *Schisandra chinensis*

Figure 17:
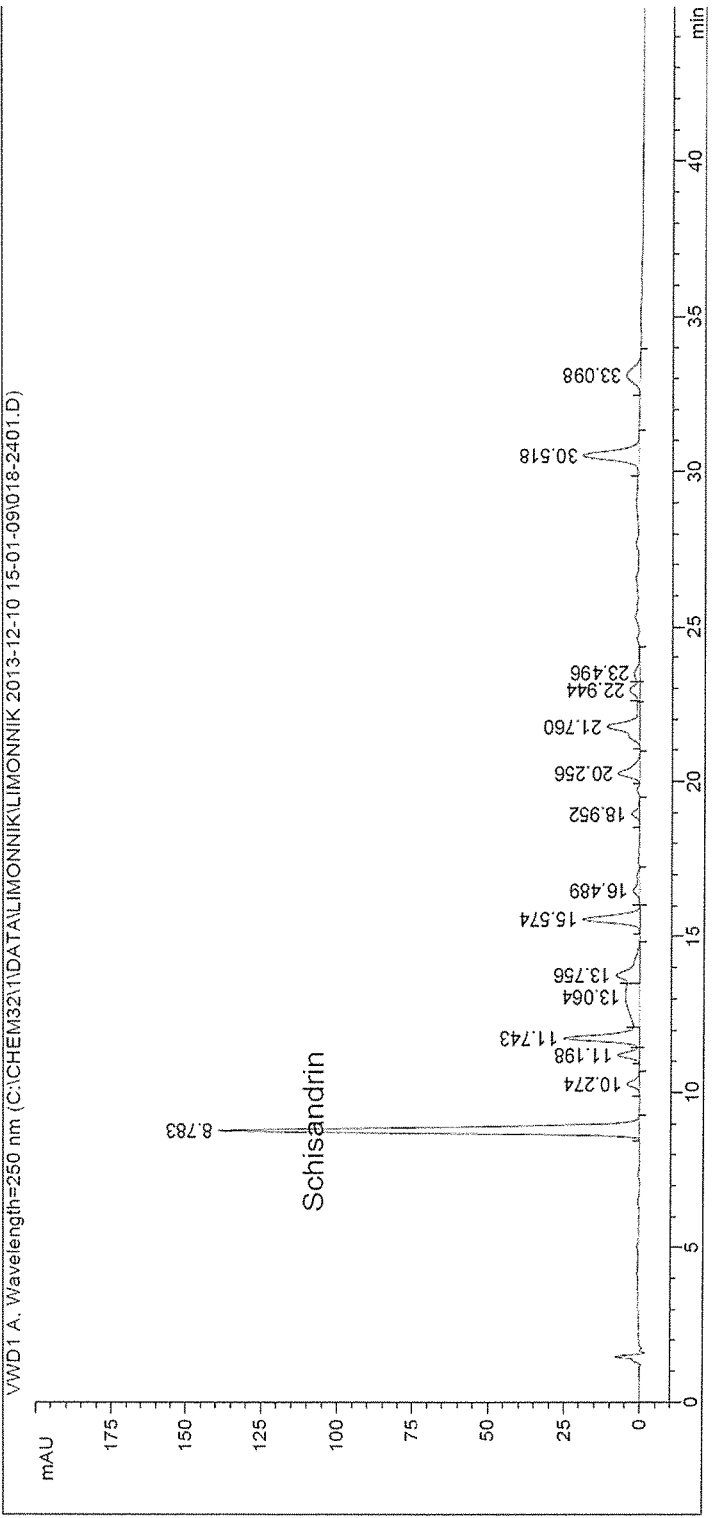
FIG. 17 is a series of Chromatograms of *Schisandra chinensis*
Figure 17:
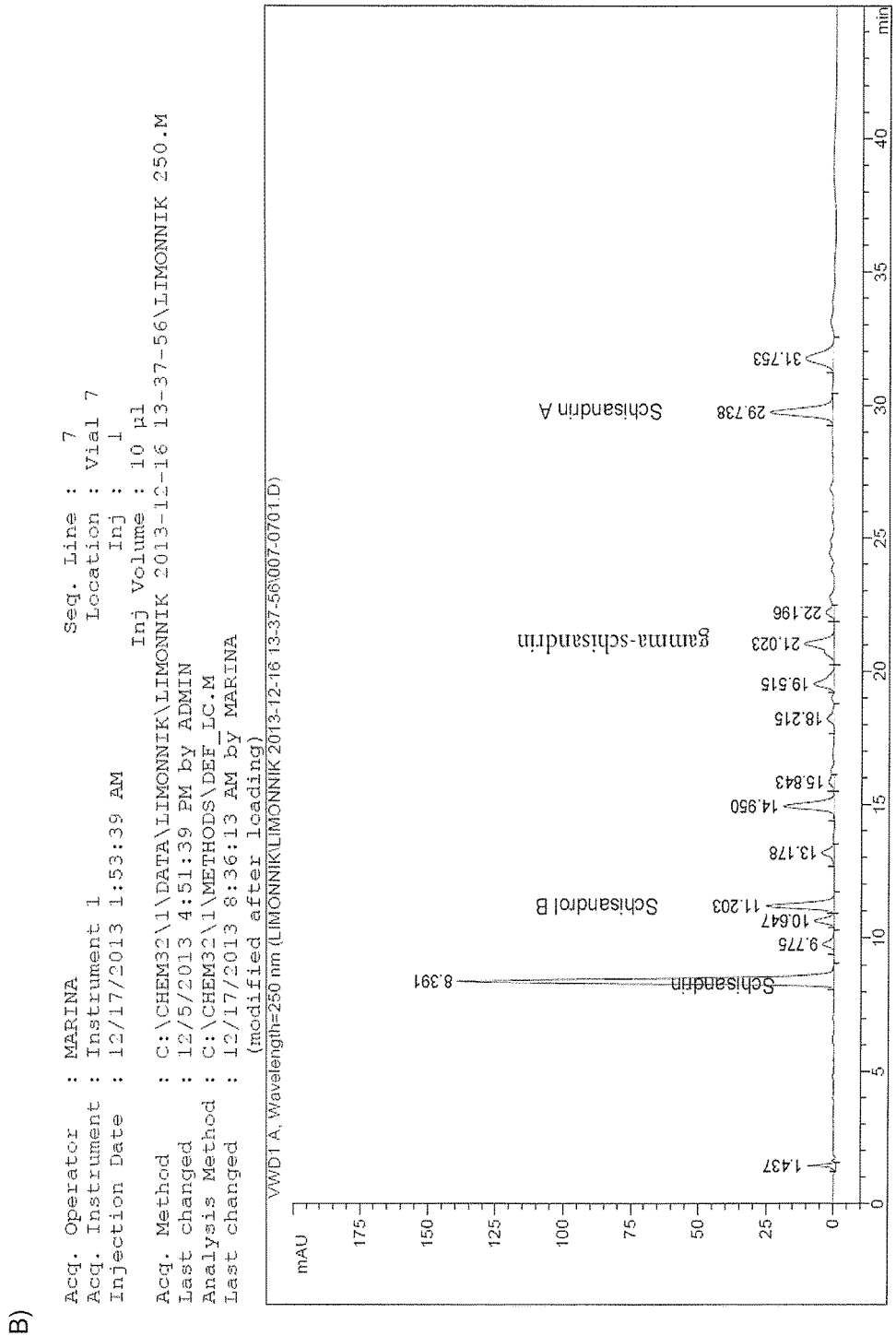

To separate, identify and quantity different compounds in a *Schisandra chinensis* seed extract the HPLC method can be used. FIG. 17 provide chromatograms of the *Schisandra chinensis* seed oil extract using HPLC methods herein disclosed (FIGS. 17A and 17B are different extractions). The detection wavelength was set at 250 nm and the injection volume of the *Schisandra chinensis* seed extract was 10 μL. Table 16 provides the area percent report which represents the area of each peak in the chromatogram as a percentage of the total area of all peaks. FIG. 17 and Table 8 show that the biological activity of *Schisandra chinensis* seeds is due mainly to lignans (group phenylpropanoid) among which schisandrin is the most abundant.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

The invention claimed is:
1. A composition comprising:
a) a liquid *Schisandra chinensis* seed oil extract comprising a standardized amount of a schisandrin compound, and
b) magnesium aluminometasilicate as an absorbent,

TABLE 16

Area Percent Report with Performance and Noise in FIG. 17A

| RetTime [min] | k' | Area mAU * s | Height [mAU] | Symm. | Width [min] | Plates | Resolution | Signal/Noise |
|---|---|---|---|---|---|---|---|---|
| 8.783 | — | 1777.52649 | 138.68454 | 0.85 | 0.1966 | 11062 | — | — |
| 10.274 | — | 61.54163 | 4.08899 | 0.90 | 0.2184 | 12259 | 4.22 | — |
| 11.198 | — | 96.80115 | 7.17534 | 0.88 | 0.2071 | 16202 | 2.55 | — |
| 11.743 | — | 382.24667 | 25.12666 | 0.84 | 0.2216 | 15552 | 1.49 | — |
| 13.064 | — | 305.49902 | 4.55386 | 1.71 | 1.2255 | 630 | 1.07 | — |
| 13.756 | — | 218.18832 | 7.51096 | 0.61 | 0.4432 | 5338 | 0.49 | — |
| 15.574 | — | 304.44354 | 18.81790 | 0.92 | 0.2475 | 21934 | 3.09 | — |
| 16.489 | — | 66.75081 | 2.15607 | 0.44 | 0.3179 | 14905 | 1.90 | — |
| 18.952 | — | 48.59386 | 2.53053 | 0.66 | 0.2621 | 28969 | 4.99 | — |
| 20.256 | — | 180.18520 | 7.25573 | 0.62 | 0.2839 | 28199 | 2.81 | — |
| 21.760 | — | 281.96826 | 10.74216 | 1.16 | 0.2985 | 29443 | 3.03 | — |
| 22.944 | — | 71.14182 | 3.29245 | 1.14 | 0.3252 | 27582 | 2.23 | — |
| 23.496 | — | 56.38216 | 1.81327 | 0.80 | 0.4756 | 13519 | 0.81 | — |
| 30.518 | — | 394.27631 | 18.48646 | 0.97 | 0.3130 | 52653 | 10.46 | — |
| 33.098 | — | 149.89230 | 4.48984 | 0.90 | 0.5145 | 22931 | 3.66 | — | wherein the standardized amount is from about 1 mg to about 10 mg per dosage unit, and wherein the composition is a solid dosage form.

2. The composition of claim 1 wherein the composition is a herbal composition, dietary supplement, or pharmaceutical composition.

3. The composition of claim 1, further comprising a filler, an additional adsorbent, a disintegrant and/or a glidant.

4. The composition of claim 3, wherein the additional adsorbent is magnesium carbonate.

5. The composition of claim 3, wherein
   a. the filler is selected from the group consisting of lactose, microcrystalline cellulose, sorbitol, magnesium carbonate, calcium carbonate, calcium phosphate dibasic and mixtures thereof;
   b. the disintegrant is selected from the group consisting of low-substituted hydroxypropyl cellulose (L-HPC), polyvinylpolypyrrolidone, potato starch, sodium starch glycolate, wheat starch, maize starch, rice starch, sodium carboxymethylcellulose, calcium carboxymethylcellulose, and mixtures thereof; and/or
   c. the glidant is selected from the group consisting of talc, fumed silica, starch, magnesium stearate, polyethylene glycol and mixtures thereof.

6. The composition of claim 1, wherein the standardized amount is from about 2 mg to about 8 mg per dosage unit, from about 3 mg to about 5 mg per dosage unit, or is about 1 mg, about 2 mg, about 3 mg, about 4 mg, about 5 mg, about 6 mg, about 7 mg, about 8 mg, about 9 mg, or about 10 mg per dosage unit.

7. A method of preparing the composition according to claim 1, comprising the steps:
   a. obtaining a standardized amount of a liquid *Schisandra chinensis* seed oil extract;
   b. mixing the standardized amount of liquid *Schisandra chinensis* extract with magnesium aluminometasilicate to obtain a mixture with a homogenous distribution;
   c. adding one or more additional excipients to the mixture comprising the *Schisandra chinensis* extract and the magnesium aluminometasilicate; and
   d. compounding the excipient-mixture into a solid dosage form.

8. The method of claim 7, wherein the solid dosage form is a soft capsule.

9. The method of claim 7, wherein the one or more additional excipients comprises a filler, an additional adsorbent, a disintegrant and/or a glidant.

10. The method of claim 9, wherein
    a. the filler is selected from the group consisting of lactose, microcrystalline cellulose, sorbitol, magnesium carbonate, calcium carbonate, calcium phosphate dibasic and mixtures thereof;
    b. the additional adsorbent is magnesium carbonate;
    c. the disintegrant is selected from the group consisting of low-substituted hydroxypropyl cellulose (L-HPC), polyvinylpolypyrrolidone (also known as crospovidone), potato starch, sodium starch glycolate, wheat starch, maize, rice, sodium carboxymethylcellulose, calcium carboxymethylcellulose, and mixtures thereof; and/or
    d. the glidant is selected from the group consisting of talc, fumed silica, starch, magnesium stearate, polyethylene glycol and mixtures thereof.

11. The method of claim 7, wherein the standardized amount is from about 2 mg to about 8 mg per dosage unit, from about 3 mg to about 5 mg per dosage unit, or is about 1 mg, about 2 mg, about 3 mg, about 4 mg, about 5 mg, about 6 mg, about 7 mg, about 8 mg, about 9 mg, or about 10 mg per dosage unit.

12. A method for providing an adaptogenic and tonic effect, increasing antioxidant activity, reducing lipid peroxidation, improving symptoms of depression, decreasing stress, increasing physical activity, decreasing blood glucose level and/or for decreasing bilirubin level in a subject in need thereof comprising administering to the subject the composition of claim 1.

13. The method of claim 12, wherein the composition is administered daily.

14. The method of claim 12, wherein the composition is administered for about 10 days to about 30 days.

15. The composition of claim 9, wherein the solid dosage form is a soft capsule.

16. The composition of claim 1, wherein the *Schisandra chinensis* extract comprises at least 4% schisandrin compound weight/weight.

17. The composition of claim 1, wherein the *Schisandra chinensis* seed oil extract is obtained using liquefied carbon dioxide at a supercritical pressure of about 100 bar to about 800 bar and a temperature of about 30° C. to about 100° C.

18. The composition of claim 1, wherein the schisandrin compound is standardized using high performance liquid chromatography.

\* \* \* \* \*

UNITED STATES PATENT AND TRADEMARK OFFICE
CERTIFICATE OF CORRECTION

PATENT NO. : 9,662,367 B2
APPLICATION NO. : 14/815243
DATED : May 30, 2017
INVENTOR(S) : Viktar Farber et al.

It is certified that error appears in the above-identified patent and that said Letters Patent is hereby corrected as shown below:

In the Claims

Column 28, Line 34, in Claim 15, delete "claim 9," and insert -- claim 1, --.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*